(12) United States Patent  (10) Patent No.: US 8,521,563 B2
Severin  (45) Date of Patent: Aug. 27, 2013

(54) SYSTEMS AND METHODS FOR MANAGING AT-HOME MEDICAL PREVENTION, RECOVERY, AND MAINTENANCE

(75) Inventor: Steven Bradley Severin, La Jolla, CA (US)

(73) Assignee: Digital Healthcare Systems, San Diego, CA (US)

( * ) Notice: Subject to any disclaimer, the term of this patent is extended or adjusted under 35 U.S.C. 154(b) by 319 days.

(21) Appl. No.: 12/898,323

(22) Filed: Oct. 5, 2010

(65) Prior Publication Data

US 2011/0087501 A1  Apr. 14, 2011

Related U.S. Application Data

(60) Provisional application No. 61/249,964, filed on Oct. 8, 2009.

(51) Int. Cl.
*G06F 19/00* (2011.01)

(52) U.S. Cl.
USPC ............................................................. 705/3

(58) Field of Classification Search
USPC ..................... 705/3, 2, 22; 600/439; 514/1.4
See application file for complete search history.

(56) References Cited

U.S. PATENT DOCUMENTS

| 7,056,289 B2 | 6/2006 | Kasper et al. |
| 2002/0077549 A1* | 6/2002 | Davidson et al. ............. 600/439 |
| 2002/0107178 A1* | 8/2002 | Van Den Berghe ............... 514/3 |
| 2002/0188513 A1* | 12/2002 | Gil et al. ......................... 705/22 |
| 2004/0078220 A1 | 4/2004 | Jackson |
| 2004/0181433 A1 | 9/2004 | Blair |
| 2004/0193448 A1 | 9/2004 | Woodbridge et al. |
| 2004/0243444 A1* | 12/2004 | Steusloff et al. .................. 705/2 |
| 2005/0065813 A1 | 3/2005 | Mishelevich et al. |
| 2005/0192848 A1 | 9/2005 | Kozminski et al. |
| 2007/0214002 A1 | 9/2007 | Smith et al. |
| 2009/0076852 A1* | 3/2009 | Pierson et al. .................... 705/3 |

OTHER PUBLICATIONS

Article, "Outpatient Management of Chronic Diseases Using the TeleWatch Patient Monitoring System," by James G. Palmer and Jeffrey A. Spaeder, Johns Hopkins APL Technical Digest, vol. 25, No. 3 (2004), pp. 253-260.

Internet advertisement for Cybernet Medical's MedStar Disease Management Data Collection System, Monitoring Outpatient Care, Jan. 1, 2003.

* cited by examiner

*Primary Examiner* — John Pauls
(74) *Attorney, Agent, or Firm* — Kyle M. Pendergrass

(57) ABSTRACT

A web-based method implemented by at least one computing device for automating a medical treatment plan is described. Content related to a program that is associated with a medical treatment is identified. The identified content is digitized. The digitized content is stored in a database. The identified content is provided to a patient via a user interface to assist the patient who is associated with the medical treatment.

47 Claims, 21 Drawing Sheets

After-care System
Your personal navigator to a successful & full discovery

Home | About Us ▾ | Patient Portal ▾ | Doctor Portal ▾ | Patient Recovery Resources ▾ | Contact Us Administrator

Page Menu
- My Recovery ▸
- Calendar
- Tracker ▸
- Videos

My Tracker

Aug 27 | 08:25 AM
Last Updated on Thursday, 27 August 2009 08:39

| | Date | Time | Duration | Exercise | Status |
|---|---|---|---|---|---|
| | Today | 8:00AM | 30Minutes | Walking Program | Complete |
| | Today | 2:00PM | 15Minutes | Medications | Complete |
| | 11/17/09 | 8:00AM | 20 Minutes | Stretching & Exercise | Incomplete |
| | 11/17/09 | 2:00PM | 30Minutes | Incision Care | Incomplete |
| | 11/21/09 | 8:00AM | 20Minutes | Nutrition | Incomplete |
| | 11/21/09 | 2:00PM | 15Minutes | Walking Program | Incomplete |
| | 11/19/09 | 8:00AM | 20Minutes | Walking Program | Incomplete |
| | 11/19/09 | 2:00PM | 15Minutes | Inflammation care | Incomplete |
| | 11/21/09 | 2:00PM | 30Minutes | Walking Program | Incomplete |

Next Exercise
Date     Today
Time     8:00AM
Duration 30 Minutes
Name     Walking Program
Difficulty Beginner
Notes
Suspend....

MyAftercare http://www.myaftercare.net/patient/

::: Dashboard ✚ Program 🗄 Network ☐ Board ✉ Messages ▼ More > John Smith | For Emergencies Call 888-123-4567 | ✕ Sign Out

Patient Header

My Activity List — Monday, 12/11-2011

| | | | |
|---|---|---|---|
| Missed | 9:00 AM | Take Your Medicine | Y N |
| Overdue | 10:00 AM | Stretching | Y N |
| Complete | 11:00 AM | Incision Care | Y N |
| Ready | 12:00 PM | & Exercise | Y N |
| Ready | 2:00 PM | Walking | Y N |
| Not Ready | 4:00 PM | Medicine | Y N |
| Not Ready | 6:00 PM | PEP Breathing | Y N |
| Not Ready | 7:00 PM | Daily Symptom Survey | Y N |

Previous | Today | Next

My Program Overview 🔍 See More
You're now in phase 3 of your recovery. Which is the most important of your recovery.
Major Risk Symptoms - click for details:
▲ Bowel obstruction ▲ Stoma
▲ Dehydration ▲ Steroid Withdrawal
▲ Wound Infection ▲ Surgical Infection

My Alerts and Medsages ➕ Get Help
12/12/2010: You have an upcoming appointment on 12/15 at 3:45 with Dr.... ⊗
12/11/2010: Alan Johnson wrote on your board: Hey John, I hope all is well with.... ⊗
12/10/2010: CCF Responded to your question: Hello Mr. Smith, You have nothing.... ⊗

My Progress Summary 🔍 See More
Progress ▮▮▮▮▮▮▮▮▯▯ 66%
You have 18 days left in your program

SYSTEMS AND METHODS FOR MANAGING AT-HOME MEDICAL PREVENTION, RECOVERY, AND MAINTENANCE

CROSS REFERENCE TO RELATED APPLICATIONS

This application claims priority to U.S. Provisional Patent Application No. 61/249,964, filed on Oct. 8, 2009, the entire disclosure of which is incorporated herein by reference.

BACKGROUND

Healthcare systems across the globe experience quality assurance issues regarding the success of a patient's recovery after that patient receives medical treatment and leaves the supervision of a medical facility. Post-treatment, at-home medical care is not only an underserved market, but is largely antiquated, cumbersome and based in an analog world. The breakdown of medical care during post-treatment, at-home recovery has resulted in unnecessary financial costs for hospitals, patients, and insurance providers. More importantly, the breakdown has led to other health-care related problems.

Methods for administering post-treatment, at-home medical care typically involve a cumbersome printed manual of instructions that can include outdated or obsolete information. These printed manuals lack structure and an interactive element that would allow a patient to easily access relevant information. Moreover, the printed manuals cannot present information in multiple formats.

Typical methods for administering post-treatment, at-home medical care also lack interaction between medical professionals and the patients, often creating a lack of accountability. An absence of communication between patient and provider after a treatment results in a missed opportunity for additional instruction and encouragement. Patients often fail to complete their recovery programs, which may lead to further injury and re-admission into a medical facility for further treatment. Accordingly, benefits may be realized by providing systems and methods for managing at-home medical prevention, recovery, and maintenance.

SUMMARY OF THE INVENTION

According to one embodiment, a web-based method implemented by at least one computing device for automating a medical treatment plan is described. Content related to a program that is associated with a medical treatment is identified. The identified content is digitized. The digitized content is stored in a database. The identified content is provided to a patient via a user interface to assist the patient associated with the medical treatment.

In one embodiment, the identified content related to the program may include an activity for the patient to complete. A status update relating to the patient's progress to complete the activity may be received. In one example, a patient record associated with the patient may be updated in response to the status update. A notification may be provided to a provider and/or a patients personal support network, such as a family member, caretaker, friend, etc. of the medical treatment relating to the updated patient record.

In one configuration, data relating to the patient's progress with the program may be collected. The collected data may be analyzed using at least one predefined algorithm, at least one predefined metric, or historical data. The results of the analysis may be provided to a third party associated with the medical treatment. In one embodiment, the third party may be a provider of the medical treatment, a physician that performs the medical treatment, or an insurance provider associated with the patient.

In one embodiment, a notification may be provided to the patient in real time relating to the medical treatment and the program. In addition, a notification may be provided to a patient support network of the patient in real time relating to the medical treatment and the program of the patient. Further, a notification may be provided to a provider in real time relating to the medical treatment and the program of the patient.

In one example, a calendar may be provided. The calendar may include at least one activity or task for the patient to complete. The recovery program may be automatically generated for the patient. At least one patient support network tool may be provided. The tool may provide information to a member of the patent support network to prepare the member to assist the patient to engage the program.

A computing device configured to provide access to a web-based application to automate a medical treatment plan is also described. The computing device may include a processor and memory in electronic communication with the processor. The web-based application may be configured to identify content related to a program that is associated with a medical treatment, and digitize the identified content. The web-based application may further be configured to store the digitized content in a database, and provide the identified content to a patient via a user interface to assist the patient associated with the medical treatment.

A computer-program product for automating a medical treatment plan is also described. The computer-program product may include a computer-readable medium having instructions thereon. The instructions may include code programmed to identify content related to a program that is associated with a medical treatment, and code programmed to digitize the identified content. The instructions may further include code programmed to store the digitized content in a database, and code programmed to provide the identified content to a patient via a user interface to assist the patient associated with the medical treatment.

A web-based method implemented by at least one computing device for interacting with a user engaging a plan associated with a medical treatment is also described. Information may be displayed to the user relating to the plan, wherein the information comprises details for at least one activity assigned to the user. Status information may be received from the user for the at least one activity. The status information may be processed. A record for the user may be updated based on the processed status information.

A web-based method implemented by at least one computing device for monitoring progress of a user in relation to a plan associated with a medical treatment is also described. Data relating to the user's progress may be collected. The collected data may be stored in a database. The collected data may be analyzed. A status report regarding the progress of the user in relation to the plan may be generated based on the analysis of the collected data. The status report may be displayed to at least one additional user who is monitoring the progress of the user.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

BRIEF DESCRIPTION OF THE DRAWINGS

The accompanying drawings illustrate a number of exemplary embodiments and are a part of the specification.

FIG. 3B illustrates another embodiment of the user interface that may be provided to the user interacting with the present systems and methods;

FIG. 4A illustrates one embodiment of an instructional tool to provide additional information to the user;

FIG. 6 illustrates one embodiment of a user interface for displaying tracking metrics that detail the progress of the user with the recovery program;

FIG. 8 illustrates one embodiment of a user interface that may be presented to the user upon logging into a service that provides the recovery program;

Figure 1:
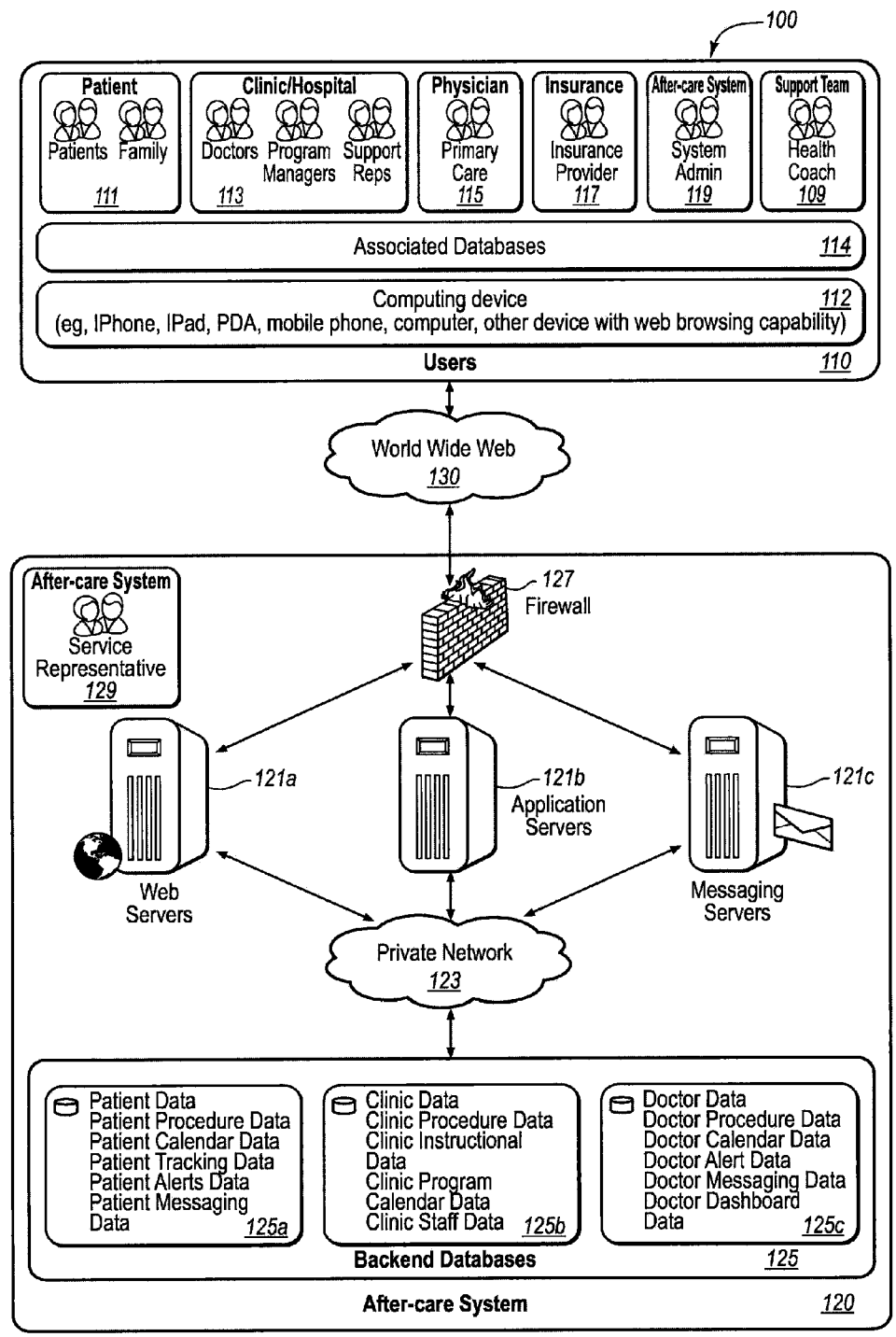
FIG. 1 illustrates one embodiment of a block diagram depicting a network system that may implement the present systems and methods.

While the embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION OF EMBODIMENTS OF THE INVENTION

Aspects of the present systems and methods may be described in the general context of computer-executable instructions, such as program modules, being executed by a computer or server. Generally, program modules include routines, programs, objects, components, data structures, and the like that perform particular tasks or implement particular abstract data types. The present systems and methods may also be practiced in distributed computing environments where tasks are performed by remote processing devices that are linked through a communications network. In a distributed computing environment, program modules may be located in both local and remote computer-readable storage media including memory storage devices.

While the details of the embodiments of the present systems and methods may vary and still be within the scope of the claimed invention, FIG. 1 illustrates a block diagram depicting a network system 100 for implementing at least one embodiment of the present systems and methods. The network system 100 is only one example of a suitable computing environment and is not intended to suggest any limitation as to the scope of use or functionality of the present systems and methods. In addition, the network system 100 should not be interpreted as having any dependency or requirement relating to any one or combination of components illustrated in the network system 100. Various intermediary network routing and other elements between various components in the network system 100 depicted in FIG. 1 have been omitted for the sake of simplicity.

Various configurations of the network system 100 may exist. For example, the network system 100 may be configured to include one or more users 111, 113, 115, 117, 119, 109 and an after-care system 120 that may send and receive information via a network connection, such as, but not limited to, the World Wide Web (WWW) 130.

Users of the system 120 may include a patient 111 undergoing treatment and recovery for an ailment, a provider 113 providing the treatment and monitoring the recovery, a primary care physician 115 who referred the patient 111 to the provider 113, an insurance company or agent 117 providing insurance payments in relation to the treatment and recovery, members of a support team 109 to support the patient 111 undergoing the treatment and recovery. The support team 109 may receive instructions via a support network user interface regarding ways to support the patient undergoing the treatment and recovery. A system administrator 119 may control the services offered by the after-care system 120 (e.g., developing and maintaining computer programs, managing access rights, etc.). The users 111, 113, 115, 117, 119, 109 may use a computing device 112 to access the services of the after-care system 120. In one embodiment, the computing device 112 may include a personal computer (PC), a laptop, a smartphone, a personal digital assistant (PDA), an iPad, or any other computing device capable of communicating with the after-care system via the network connection 130. Some or all of the users 111, 113, 115, 117, 119, 109 may be associated with one or more databases 114 that store information relating to the services offered by the after-care system 120. The databases 114 are described herein in several implementations as hard disk drives for convenience. Other storage media may be utilized as a database without departing from the scope of the present systems and methods. The information stored in the databases 114 may represent patient records, insurance policy information, doctor notes, hospital policies, treatment and recovery procedures, or various other representations of information in accordance with the present systems and methods. A database 114 under the control of one user (e.g., the provider 113) may be configured to allow the after-care system 120 or other users (e.g., the insurance provider 117) to access some or all of the information stored therein. Alternatively, as described in further detail below, the information stored in and accessed from the databases 114 may instead be stored in and accessed from backend databases 125a, 125b, 125c within the after-care system 120.

In one embodiment, the after-care system 120 may include one or more load-balanced servers 121a, 121b, 121c to host one or more web-based applications of general computer applications. The after-care system 120 may further include a private network 123 to connect the servers 121a, 121b, 121c to the backend databases 125a, 125b, 125c, and a firewall 127 to control the exchange of data between the network connection 130 and the various components of the after-care system 120. The after-care system 120 may also include one or more service representatives 129 (e.g., a programmer, system administrator) that perform various functions described below. The service representatives 129 may perform many of the automated functions described below, and that computer applications may automatically perform many of the functions of the service representatives 129 and users 111, 113, 115, 117, 119, 109.

In one example, a first server 121a may be a web server. A second server 121b may be an application server. A third server 121c may be a messaging server. The messaging server 121c may distribute/receive messages to/from specific users 111, 113, 115, 117, 119, 109. In one embodiment, at least a portion of the messaging traffic may pass through the firewall 127. Each server 121a, 121b, 121c may communicate with the databases 125a, 125b, 125c over the private network 123. The private network 123 may include bus architectures, area networks, and the like.

In one configuration, the databases 125a, 125b, 125c may include information to implement the functionality of various embodiments of the present systems and methods. For example, a first database 125a may include patient data (e.g., data relating to a patient's registration with the after-care service 120, ailment data, treatment data, recovery and messaging data), a second database 125b may include provider data (e.g., data relating to a provider's registration with the after-care service 120, data relating to the treatment of any number of ailments for any number of patients, data relating to recovery assistance plans/recommendations, general policies, and messaging data), a third database 125c may include medical personnel data (e.g., data relating to notes from a doctor/nurse regarding treatment and recovery associated with any number of patients and messaging data), a fourth database (not shown) may include insurance data, and a fifth database (not shown) may include system administration data.

In one embodiment, the after-care system 120 may be designed as a Software-as-a-Service (SaaS) system that supports multiple users 111, 113, 115, 117, 119, 109 from a single location that houses all necessary hardware, software, and devices. Under this configuration, all of the data may be stored in the databases 125a, 125b, 125c. As a result, the databases 114 associated with the various users 111, 113, 115, 117, 119, 109 may not be necessary. In one example, the data stored in the databases 125a, 125b, 125c may be separated according to the various users 111, 113, 115, 117, 119, 109 (e.g., on a per provider basis, a per patient basis, a per doctor basis, a per primary care physician basis, a per insurance provider basis, or any combination thereof and/or any variations thereof). By isolating the data according to users, the present systems and methods may comply with the Health Insurance Portability and Accountability Act (HIPAA) privacy standards and requirements. In addition, data may be organized to allow for data analysis of any number of users 111, 113, 115, 117, 119, 109. For example, within each dataset associated with a provider 113, information representing treatment procedures and recovery programs offered by the provider 113 may be defined. In addition, each provider 113 dataset may define patients 111, their particular treatment procedure, and their recovery plan (e.g., a schedule of activities, descriptions of those activities, and supporting materials, such as, but not limited to, video demonstrations and background material).

In accordance with at least one embodiment, the after-care system 120 may distribute/receive information to/from the users 111, 113, 115, 117, 119, 109 via various forms of messaging (e.g., email, short messaging services (SMS), audio phone messages, etc.). The messaging may be carried out using standard email clients such as Microsoft Outlook, MacMail, etc., web browsing in connection with email clients such as GMail and Yahoo!Mail, etc., cellular network data exchange technologies, and other forms of communicating information. The messaging, along with other data exchange and associated data storage, may be carried out in compliance with HIPAA privacy standards and requirements.

Certain embodiments of the present systems and methods relate to a process for registering a user 111, 113, 115, 117, 119, 109 with the after-care system 120 in order to allow that user to upload, access, or monitor an online recovery program associated with the treatment of a patient's 111 ailment.

Figure 2:
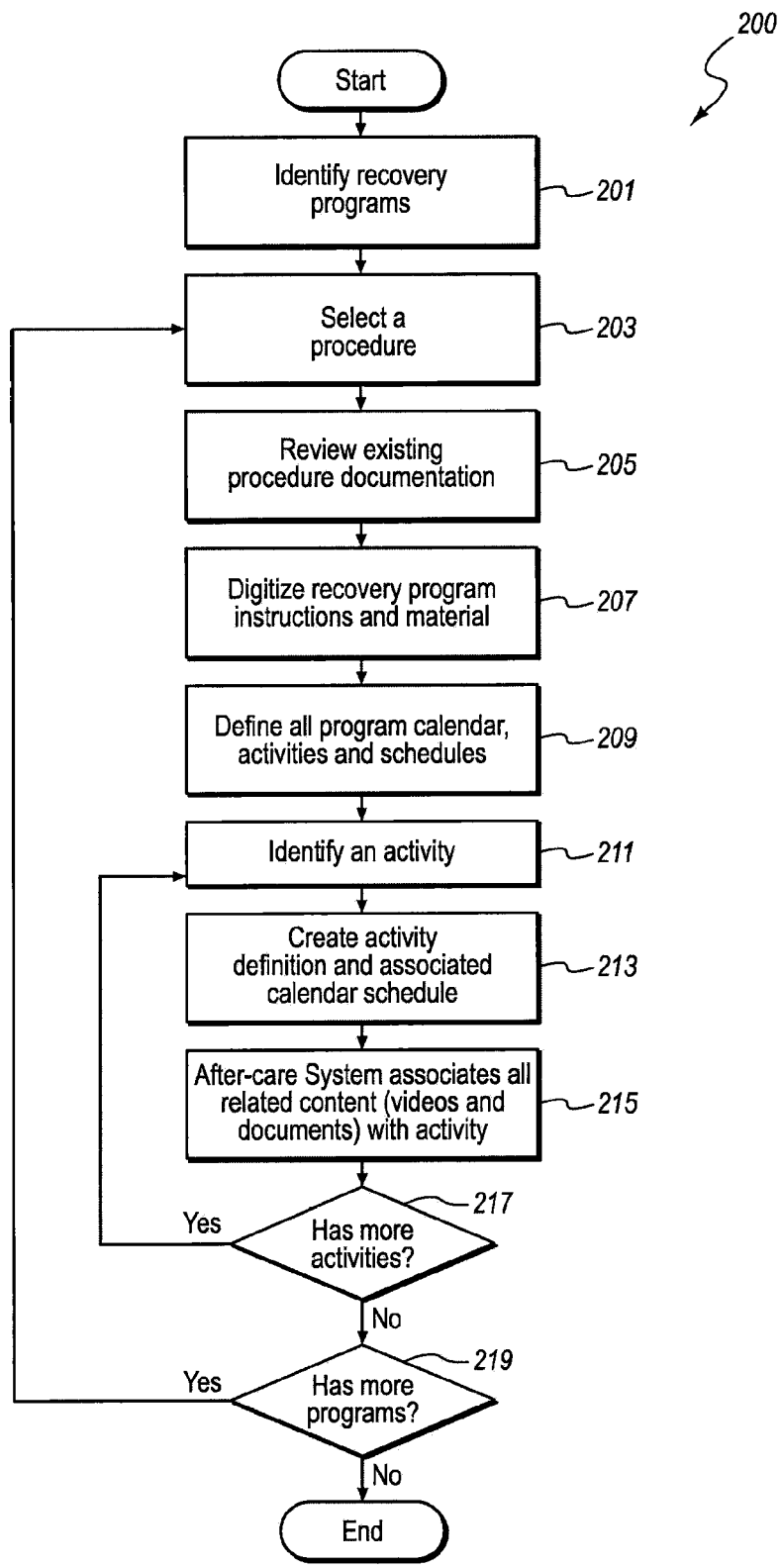
FIG. 2 is a flow chart illustrating one embodiment of a method for registering with an at-home medical prevention, recovery, and maintenance system in accordance with the present systems and methods.

FIG. 2 illustrates a flow chart illustrating one embodiment of a method 200 for registering a provider 113 with the after-care system 120. While referring to FIG. 2, simultaneous reference is made to FIG. 1. In one embodiment, the method 200 may be implemented by the after-care system 120.

In one configuration, recovery programs that the provider 113 offers to patients 111 may be identified 201. At least one identified recovery program may be selected 203.

Existing materials associated with the selected at least one recovery program may be reviewed 205. For example, existing materials may include printed documents, online documents, booklets, videos, calendars, knowledge of a person associated with either the provider 113 or the recovery program, and any other form of instructional materials made available by the provider 113 to guide the patient 111 during his or her recovery after a treatment of an ailment.

Once the materials have been reviewed, the materials may be converted 207 into digital form. The conversion may include activities such as, but not limited to, digitization of static images through scanning, typing, document transfer, and recreation of documents in various digital formats. The conversion may also include digitization of video and audio recordings that include instructions for carrying out a particular selected recovery program. The digitized information may be stored in the databases 125a, 125b, 125c for use within a content library for that particular provider 113. In another embodiment, the digitized information may also be stored in any other database (e.g., the database 114 associated with the provider 113).

Each recovery program that is selected for implementation in the after-care service may include a preparation phase that relates to tasks performed by the patient 111 prior to a treatment procedure, a recovery phase, that relates to tasks performed by the patient 111 immediately after the treatment procedure, and a maintenance phase that relates to tasks performed by the patient 111 after recovery has completed. Any of the preparation, recovery, and maintenance phases may be customized to the needs or preferences of the patient 111 or the unique results of the treatment. Alternatively, any of the phases may be partially or entirely based upon a standard program for that type of treatment.

In one embodiment, a recovery program calendar may be defined 209 that specifies the schedule for some or all of the recovery activities assigned to the patient 111. A particular activity may be identified 211 (e.g., stretching the patient's 111 legs, taking a 15 minute walk, taking medicine, etc.). Each identified activity may be given a description and assigned 213 one or more non-reoccurring or reoccurring dates and times for completion by the patient 111. For example, a patient 111 may be required to stretch for 15 minutes, 3 times a day, for 7 days a week for the first two weeks of his or her recovery, starting on July 2. The stretching activity may be defined with the name of the activity (e.g., "stretching" or "stretching for 15 minutes") and the time (either a specific time or a block of time) that the activity is scheduled (e.g., each of the first 14 days of the recovery at three specified times during each of those days). The definition may also include an indication of the importance and significance of the activity (e.g., "required" or "recommended"). As is described in further detail below, the importance/significance of the activity may determine whether, and to whom, an alert or warning is sent if the patient 111 fails to complete the scheduled activity. For example, failure to complete a required activity may produce an alert message that is sent to a doctor associated with the provider 113, who may contact the patient 111. Alternatively, failure to complete a recommended activity may produce a warning that is sent to the patient 111 along with additional information regarding the value in completing the activity. In addition, an alert message may be produced that is sent to a nurse associated with the provider 113 who then determines whether to follow up with the patient 111.

In one embodiment, content and instructional materials associated with each defined recovery program activity may be identified 215. At least a portion of the identified content and instructional materials may be made available to the patients 111 in connection with the activities listed on the program calendar. A determination 217 may be made as to whether additional activities exist. If additional activities exist for a particular program, the method 200 may repeat steps 211-215 for each activity. If it is determined 217 that a program has no more activities, a determination 219 is made as to whether additional recovery programs exist. If additional programs exist, the method 200 repeats steps 203-217 for each program. If no additional programs exist, the method 200 ends.

Figure 3A:
FIG. 3A illustrates one embodiment of a user interface that may be provided to a user interacting with the present systems and methods.
Figure 3B:
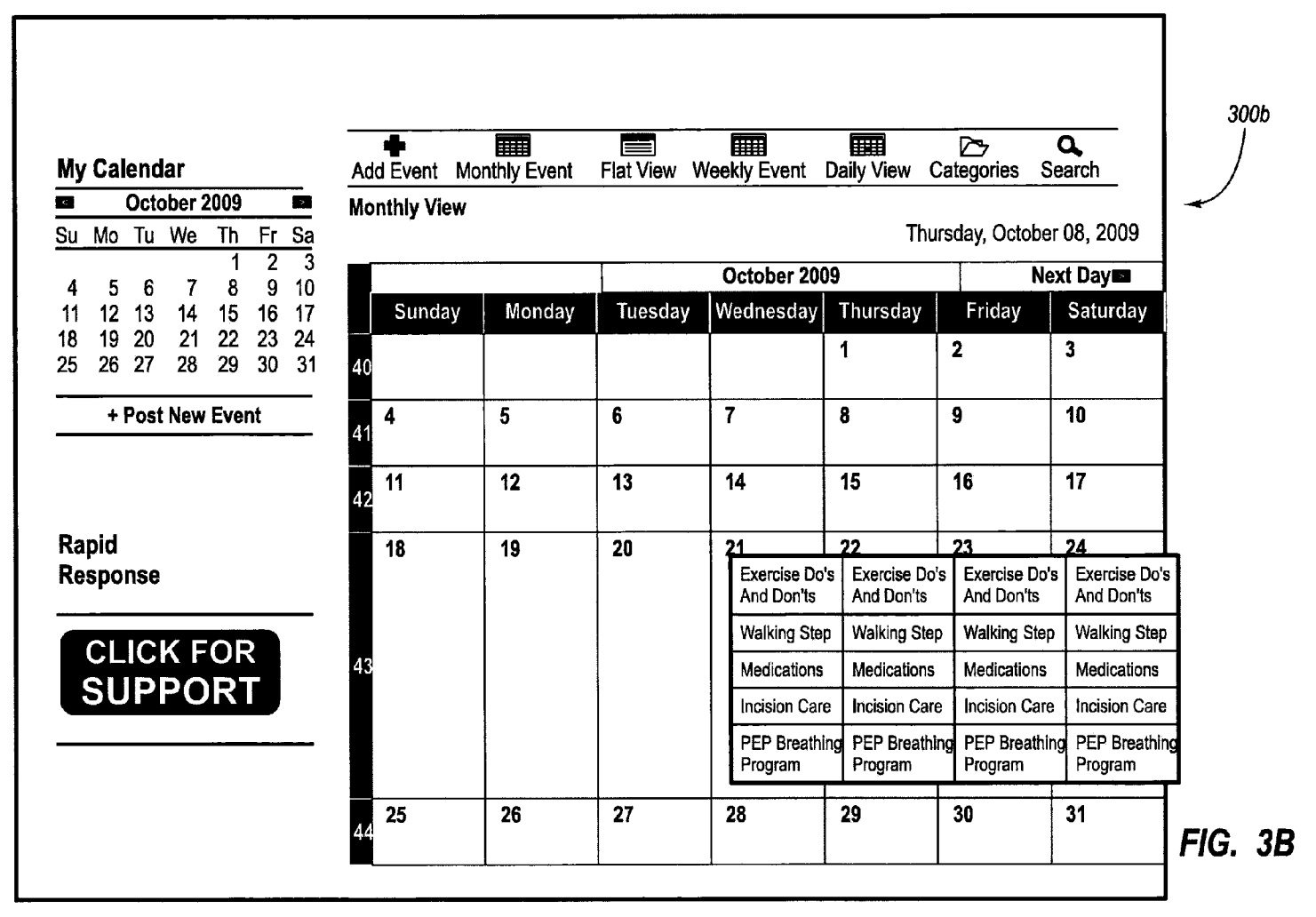

An example of a daily view of a program calendar 300a provided by the after-care service to patients 111 is illustrated in FIG. 3A. FIG. 3B illustrates one example of a monthly view of a program calendar 300b provided by the after-care to patients 111. As shown in FIG. 3A, the daily view of the program calendar provides a list of activities (e.g., "Walking Step I") and corresponding times for those activities (e.g., "8:00 AM-8:05 AM"). In addition, the program calendar 300a may identify information for the patients 111 on what to do and what not to do during their recovery (e.g., the "Do's and Don'ts"). If the patient 111 wants additional information or instruction regarding a particular activity or the "Do's and Don'ts," the patient 111 may click on the descriptions of the activities or the "Do's and Don'ts" to receive the additional information or instruction via an instructional tool associated with the calendar (e.g., via text files, video file or audio files accessible by clicking on links in the calendar or by accessing the content library).

The after-care system 120 may allow for various customizations of a patient's activity list and program calendar. This allows authorized doctors and nurses to make changes or additions to the patient's calendar to address specific needs for each individual patient (beyond the generalized recovery programs for broader groups of patients). A health provider may alter (change, remove or add) activities and medications from the patient details view within a provider portal (described below).

A patient may also make changes (additions only) to their activity list and calendar, which enables them to add their own tasks or activities to their program calendar. An example custom activity may be to call a member of their support team to share some information about their recovery. This flexibility with the patient's activity list allows the patient to manage their scheduled activities (both within their prescribed recovery and for ancillary, personal things outside of their prescribed recovery) all in one common place.

The after-care system 120 may allow patients to incorporate their recovery activities scheduled on their recovery program calendar with other forms of digital calendars though calendar integration. This integration may publish the details about scheduled activities so that other tools and products (such as, but not limited to, iPhone, desktop PC, iPads, laptops, MS Outlook, Mac Calendar, Google Calendars) may subscribe to this calendar data source and populate calendar entries on those products or devices.

Figure 4A:
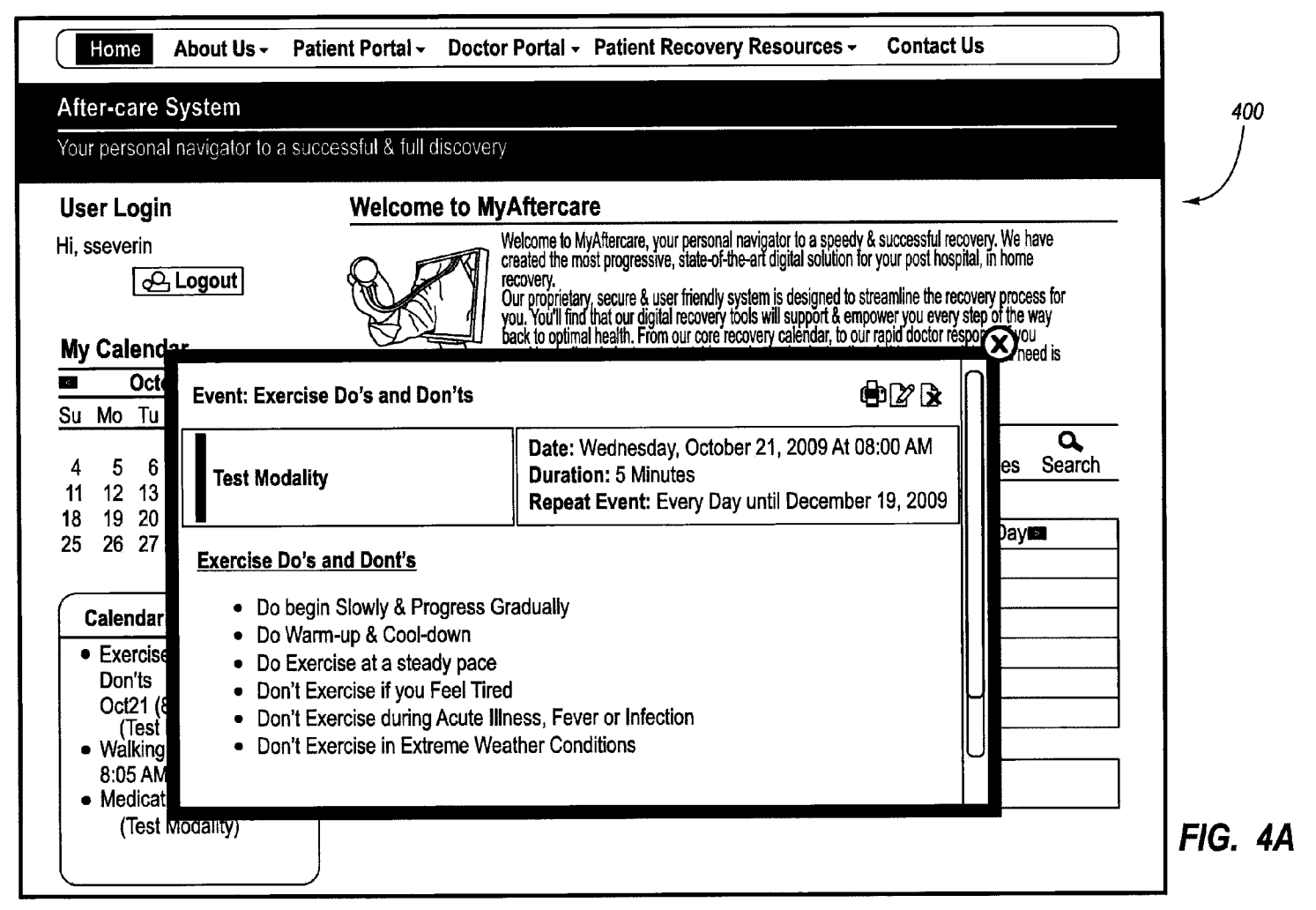

FIG. 4A illustrates one example of an instructional tool 400 that makes additional information available to the patient 111 after the patient 111 selects an activity listed in either the daily view of the program calendar 300a or the monthly view of the program calendar 300b. The patient 111 may select an activity in either view of the program calendar 300a, 300b by clicking on a link. For example, a link titled "Incision Care" is illustrated in the daily view of the program calendar 300a and the monthly view of the program calendar 300b. The link in the daily view of the program calendar 300a may include a description of the activity (e.g., "Incision Care (10:00 AM-10:15 AM") as well as a link to video instructions. The instructional tool 400 may provide additional information regarding this particular activity selected by the patient 111 from the program calendar 300a, 300b.

Figure 4B:
FIG. 4B illustrates another embodiment of an instructional tool to provide additional information to the user.

FIG. 4B illustrates another example of the instructional tool 400 that provides additional information to the patient 111 via a health library webpage. As illustrated, the instructional tool 400 may include a "Health Library" section. In one embodiment, a patient 111 may search for content across all of the content related to the patient's 111 recovery program. This may include the ability to search through instructional texts, "Do's and Don'ts" and frequently asked questions (FAQs) related to the recovery program or the activities contained within.

Certain embodiments of the present systems and methods may relate to a method for registering the patient 111 for a web-based recovery program, allowing the patient 111 to access the recovery program after his or her treatment, and monitoring whether the patient 111 satisfactorily completes his or her recovery program.

Figure 5:
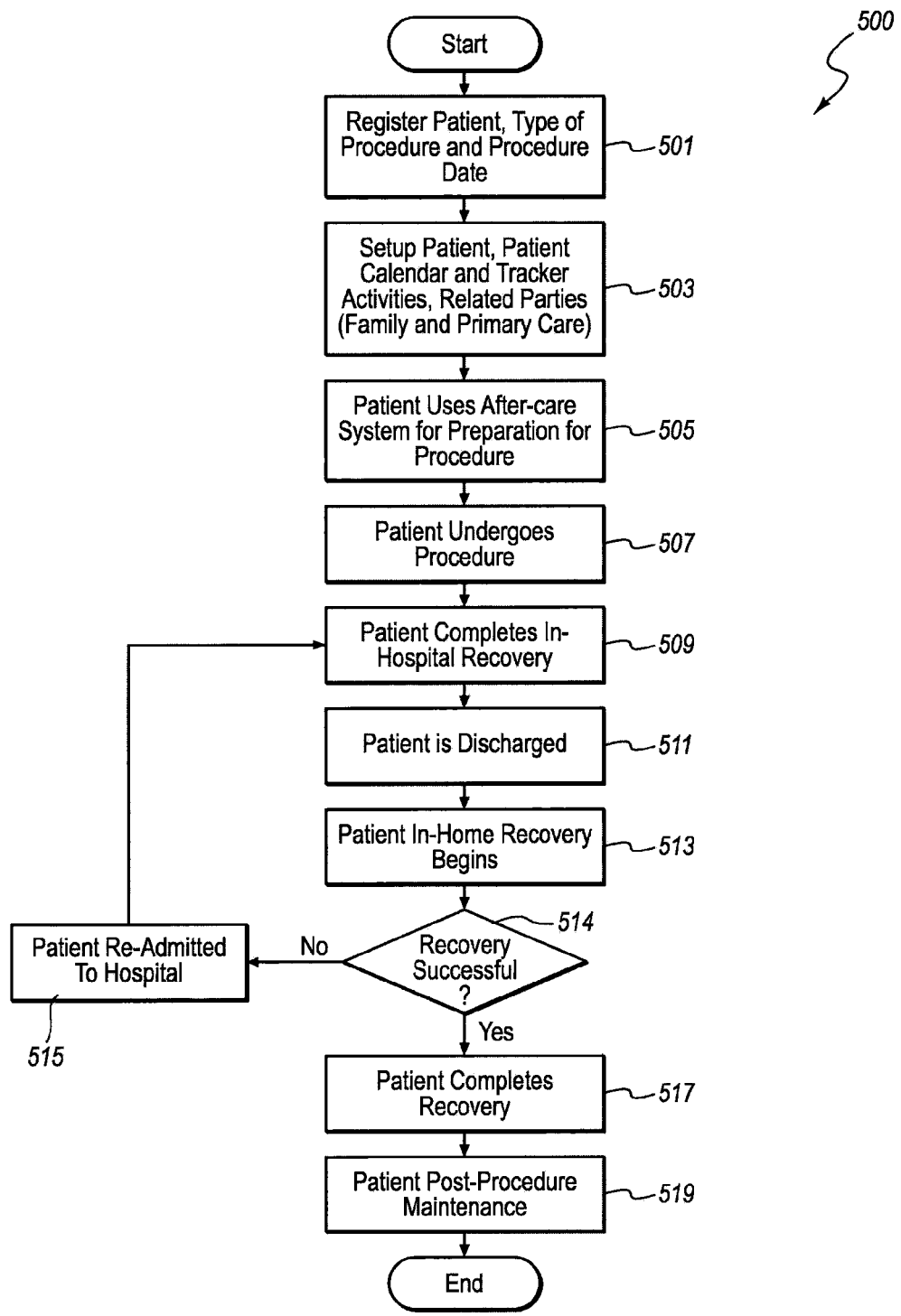
FIG. 5 is a flow chart illustrating one embodiment of a method for providing the user with a recovery program.

FIG. 5 is a flow chart illustrating one embodiment of a method 500 for providing a recovery program to a patient 111. In one configuration, the method 500 may be implemented by the after-care system 120.

In one embodiment, the patient 111 may be scheduled 501 for a treatment. The scheduling 501 may include registering the patient 111, identifying the type of treatment, and specifying the date of the treatment. Data representing the aforementioned registration, identification, and specification may be entered into the after-care system 120 by a user 110 (e.g., the patient 111, the provider 113, or a computer application). Registration information may include information about the patient 111 (e.g., name, contact info, age, weight or other physiological/biological information, etc.). This information may be used to create a new record of a recovery program in the databases 125a, 125b, 125c for the particular patient. In another embodiment, the information (e.g., weight or other physiological/biological information) may be used by the computer application to automatically select a particular recovery program or customize a preset recovery program to fit an existing condition of the patient 111 based on the patient's 111 information (e.g., if the patient 111 is overweight or has a bad hip).

A patient record may be created 503 in the databases 125a, 125b, 125c. The patient record may include a data representation of a program calendar for the patient 111 using recovery program details defined by the provider 113 and/or a computer application. An example of the process for setting recovery program details was described above in relation to FIG. 2. The activities included on the program calendar may include pre-treatment preparation activities (i.e., activities set for completion prior to the treatment in order to prepare the patient 111 for the treatment), recovery activities (i.e., activities set for completion after the treatment in order to help the patient 111 recover from the treatment), and maintenance activities (i.e., activities set for completion after recovery in order to maintain the patient's 111 health). The patient record may also include tracking metrics for monitoring the patient's 111 status during each of the pre-treatment, recovery, and maintenance stages. FIG. 6 illustrates one example of a user interface to display tracking metrics that detail the progress of the patient 111 in relation to completing or not completing assigned activities.

In one configuration, the scheduling and patient record creation processes described above may also include recording information from family members of the patient 111 in addition to recording information from other users (e.g., insurance providers 117, primary care physicians 115, etc.). The after-care system 120 may define a patient support network 109 that allows these other related users to follow the patient's 111 progress through his/her recovery. In other words, the after-care system 120 of the present system and methods may allow patients 111 and the people they depend upon to participate in their recovery program. In one embodiment, the patient 111 may include these other people in a patient support network 109. The support network 109 may include people of various personal and professional relationships to the patient 111. Individuals included in the patient support network may logon to the after-care system 120 and interact with the patient's recovery program in various capacities. In one embodiment, a helper may be a person in the support network 109 that helps the patient 111 use the after-care system 120. The person (or persons) designated as a helper may be capable of doing any and all functions that the patient 111 may perform. Examples of people who may be designated as a helper may include, but are not limited to, an at-home nurse, a care-giving family member, a care-giving friend, and the like.

A person (or persons) in the support network 109 may also be designated as a watcher. The person designated as the watcher may have "view only" capabilities as it relates to the instructional tools provided by the after-care system 120. A watcher may follow, monitor, send, and receive messages while supporting the patient 111 during the recovery period. A watcher may not track activities on behalf of the patient 111, but a watcher may receive notifications through which the watcher may follow along as the patient 111 completes the daily-prescribed recovery activities. Some examples of people that may be identified as a watcher may include, but are not limited to, a primary care physician, a family member, a friend, a neighbor, and the like.

In one embodiment, the patient 111 (or a helper for the patient 111) may add people to the support network 109 through a manage support network module within a patient module provided by the after-care system 120. The patient 111 may be presented with a list of current support network members, which shows the status of whether or not the support member has accepted their invite and the date they last accessed the patient's 111 recovery program. From that list, the patient may select, view, edit, or remove that support member from the support network. The patient 111 may also add a new support member from the manage support network module. When the patient 111 adds a support member, the patient 111 may be asked to supply identifying information for the new support member. The identifying information may include a first and last name, an email address, the relationship to the patient 111, and the role (helper or watcher) for the support member. After the patient 111 completes the process of defining the new support member, the after-care system 120 may send an email to the email address of the new support member. The invitation email may include a link that the new support member can click to access the after-care system 120 and complete the setup process as a support member for the patient 111.

In one embodiment, the patient 111 uses 505 services provided by the after-care system 120 to prepare for the treatment. Services provided to the patient 120 may include the program calendar, instructional tools associated with the calendar that are designed to educate and empower the patient 111 (and members of the support network) regarding how to complete and conduct activities listed in the calendar, the tracking user interface, and other functional aspects like sending and receiving messages to other users 110 (e.g., the provider 113, primary care physician 115).

In one configuration, the patient 111 may undergo 507 the treatment offered by the provider 113. After the treatment is complete, the patient 111 may complete 509 an in-hospital recovery. Depending on the provider 113 and type of treatment, the duration of the in-hospital recovery may be extensive (one or more days) or brief (less than a day). When the in-hospital recovery is complete, the patient 111 may be discharged 511 from the hospital.

Upon discharge, the patient 111 may begin 513 in-home recovery using the after-care system 120. In one embodiment, the patient 111 logs into the after-care service 120 using credentials that were setup for the patient 111 during scheduling 501 and patient record creation 503. In addition to the patient 111, members of a patient's support network may logon to the after-care system 120 and act on behalf of the patient 111. This may allow supporting health professionals (e.g., an at home nurse), family members, friends, and other forms of care givers to help the patient 111 use and follow the recovery protocols provided by the after-care service 111.

In one embodiment, the patient 111 may view a program calendar, which may guide the patient 111 through the day's activities and may provide the patient 111 with instructional materials (e.g., videos, documents, articles) that detail how to perform the activity and how to report whether the patient 111 completed the activities.

As the patient 111 progresses through his or her recovery program, a determination 514 may be made as to whether recovery of the patient 111 was successful. In other words, the patient 111 may either fail the recovery program (e.g., by failing to complete certain activities listed in the calendar), leading to the patient 111 being re-admitted 515 to the hospital, or complete 517 the recovery program (e.g., satisfactorily complete certain activities listed in the program calendar). The definition of success or failure in relation to completing a recovery program may be customized in relation to the needs or condition of each patient 111, each provider 113, or other user 110.

After the patient 111 successfully completes their recovery, the patient 111 may participate 519 in a post-procedure maintenance program offered through the after-care service 120. The maintenance program may be designed to support continued health through a calendar-based interface that is similar to that illustrated in FIG. 3A and described above in relation to the recovery program.

Figure 7:
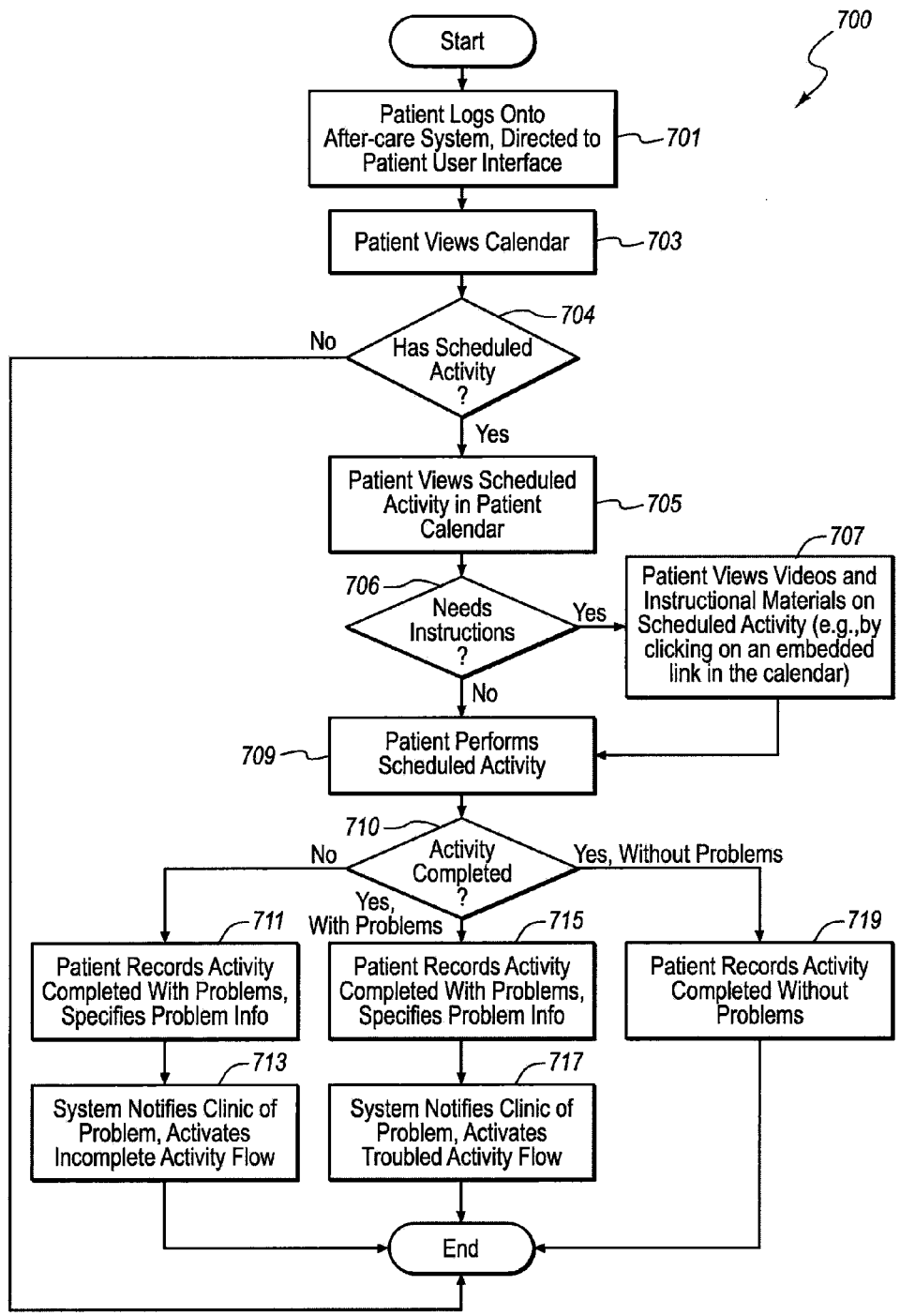
FIG. 7 is a flow chart illustrating one embodiment of a method for providing the recovery program to the user.

Certain embodiments of the present systems and methods may relate to a process for providing a recovery program to a patient 111. FIG. 7 is a flow chart illustrating one embodiment of a method 700 for providing the recovery program to the patient 111.

In one embodiment, the patient 111 logs on 701 to the after-care service 120 to receive guidance regarding daily recovery activities. The patient 111 may be directed to a patient dashboard. By way of example, FIG. 8 illustrates a patient dashboard 800 that may be presented to the patient 111 upon logging into the after-care service 120. The dashboard 800 may display portions of a program calendar along with system messages and alerts the patient 111 has received.

In one configuration, the patient 111 may access the program calendar to determine 704 if tasks have been scheduled for a particular day and time. If the patient 111 has one or more scheduled activities, the patient 111 may click on a link within the calendar to view 705 the details for the scheduled activity. A determination 706 may be made as to whether the patient 111 desires additional instructions regarding the scheduled activity. If it is determined that the patient 111 desires additional instructions, the patient 111 may select an option to view instructional videos, documents, articles and other media that guide the patient 111 to complete the scheduled activity. After reviewing the additional instructions, or if it is determined 706 that the patient 111 does not desire to view additional instructions, the patient 111 may perform 709 the scheduled activity.

A determination 710 may be made as to whether the scheduled activity is completed. For example, the patient 111 may enter the results of his or her attempt to complete the activity into the program calendar. The patient 111 may enter any of the following results: activity could not be completed 711, activity was completed with problems 715, and activity was completed without problems 719. Recording a result may be accomplished via various methods. One particular method is to select an option presented on a screen of a computing device used by the patient 111. The options may be presented via a button graphic, dropdown menu, and the like.

When the patient 111 enters some indication that an activity could not be completed 711, the patient 111 may then describe the problem that prevented the patient 111 from completing the activity. The possible details and data fields to be collected are largely determined by each provider 113, but may contain a status field in the form of a drop-down menu providing a set of pre-defined options and a text box for allowing the patient 111 to describe the details of the problem.

When the patient 111 enters some indication that an activity could be completed, but with complications 715, the patient 111 may then describe the problem that occurred while completing the activity. The possible details and data fields to be collected are largely determined by each provider 113, but may contain a status field in the form of a drop-down menu providing a set of pre-defined options and a text box for allowing the patient to describe the details of the problem.

After an incomplete activity 711 or a troubled activity 715, the after-care system 120 may notify the provider 113 or primary physician 115 of the problem via a message. Further, the personal support network of the patient may also be notified. In addition, the after-care system 120 may activate any corresponding workflow for the provider 113 or primary physician 115. Examples of such workflow are provided in greater detail in relation to FIGS. 9-12. For incomplete activities, an incomplete activity process flow is activated 713. For activities completed with problems, a troubled activity process flow may be activated 717. The details of these flows may be determined by the providers 113. Examples of such process flows are provided in greater detail in relation to FIGS. 9-12. When a patient records that an activity was completed without problems 719, the after-care system 120 may record that indication from the patient 111 in the databases 125a, 125b, 125c, or an associated database 114 associated with the patient 111.

Figure 9:
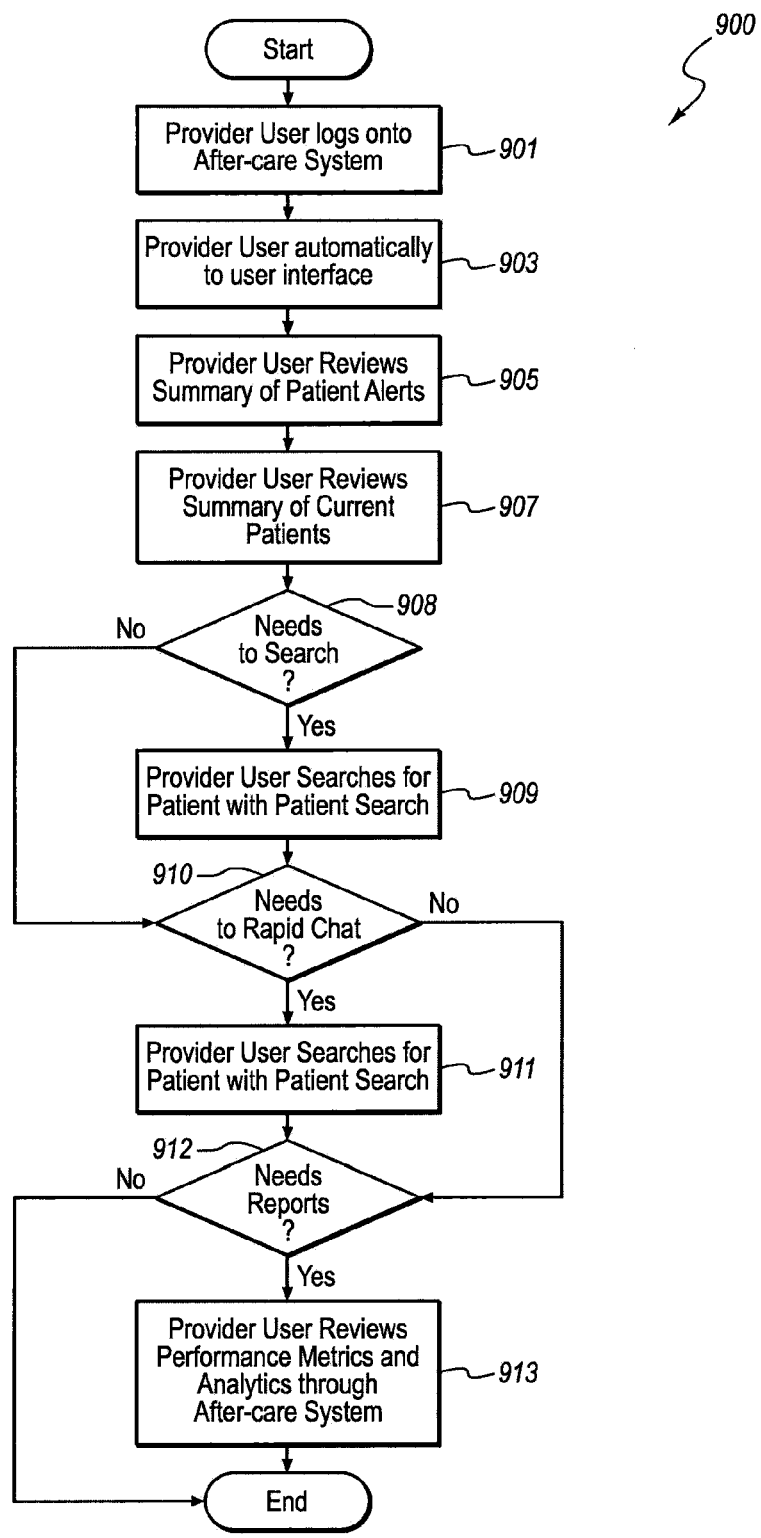
FIG. 9 is a flow chart illustrating one embodiment of a method for accessing data relating to the progress of the user in relation to the recovery program.

Certain embodiments of the present systems and methods relate to a process for allowing a provider 113 to access data related to the progress of a patient 111 in relation to a recovery program. FIG. 9 is a flow chart illustrating one embodiment of a method 900 for allowing the provider 113 to access data related to the progress of the patient 111 regarding the recovery program.

In accordance with one aspect of the present systems and methods, the provider 113 may monitor patients 111 via the after-care service 120. In particular, the after-care service 120 may provide any number of user interfaces to a provider representative of the provider 113. The provider representative may interact with one or more of these interfaces to view and manage various aspects of the recovery programs for one or more patients.

A provider user may logon 901 to the after-care service 120 through a web-based application interface. Upon successful logon, the provider user may be directed 903 to a provider dashboard user interface.

The provider user may review 905 a summary of provider tasks. The summary of provider tasks may illustrate a listing of tasks generated after patients 111 indicate a failure to complete an activity or some trouble with a completed activity. Upon viewing the tasks, the provider user may address the task (e.g., by contacting the patient 111 directly). Alternatively, the after-care system 120 may route the task to a medical professional responsible for managing the patient 111 or responding to particular tasks. In one embodiment, provider tasks may include, but are not limited to, patient enrollment, patient tracking follow-up, pending patient response, patient inactivity alerts, patient discharge, and patient completion. Additional information regarding reviewing the summary of provider tasks is provided in relation to FIG. 10.

After reviewing the summary of tasks, the provider user may review 907 the summary of any number of current patients. The provider user may view a detailed listing of the current patients and a high-level summary of status information that indicates each patient's overall status. For example, a patient 111 that has completed all activities in a timely manner without reporting any incomplete activities or trouble completing activities may be presented with a green (good) status. A patient 111 that has not reported any incomplete activities or trouble completing activities, but has not been reporting their activities in a timely manner may be presented with a yellow (warning) status. A patient 111 reporting incomplete activities or problems completing activities may be presented with a red (alert, bad) status. For further information on each patient, the provider user may click on a link representing the patient's name to view information about that patient that may be stored in the databases 125*a*, 125*b*, 125*c*. For example, the information may include the patient's program calendar and overall summary of activity.

A determination 908 may be made as to whether a search of patients is desired. If the search is desired, the provider user may use a patient search function by entering any details the provider user may have about a patient 111 (e.g., first name, last name, type of procedure, attending staff member, etc.) to search 909 for a specific record for the patient 111. The patient search may also search 909 for patients using the summary patient status, which indicates how the patient is performing within their recovery program. Searching by status feature may be useful in selecting "only the good patients", or "only the troubled patients" by using green, yellow and red status options. Green status may represent patients that are performing well with their prescribed recovery activities. Yellow status may represent patients that are experiencing some difficulties in completing their recovery activities. Red status patients may represent patients that are non-compliant with their recovery activities and possibly at risk of failing their recovery program. The search function may allow for successive searches to narrow the candidate patients. Once found, the after-care service 120 may display information relating to the patient 111. This information may be configurable depending on the needs or access rights of the provider user.

If it is determined 908 that a search is not desired, a determination 910 may be made as to whether a rapid chat session is desired. If it is determined that a rapid chat session is desired, the provider user may access a chat interface to initiate or participate 911 in a chat session with the patient or other user 110 (e.g., another medical professional at the provider 113, primary care physician 115, insurance provider 117, etc.). The interface routes incoming chat requests from the patient 111 or other users 110 to provider users and also routes outgoing chat requests from provider users to the patient 111 or other users 110. The chat interface may enable secure communications to comply with any privacy requirements.

In at least one embodiment, the chat interface may be connected to a messaging interface that handles events when one party (e.g., either the provider 113 or the patient 111) attempts to communicate with the other party while the other party is not actively interfacing with the after-care service 120. Under these circumstances, the messaging interface may notify the initiating party that the receiving party is unavailable and may present the initiating party with an interface to construct a one-way message for the receiving party (e.g., a message similar to an email). Each message and chat may be saved for auditing, tracking, and analysis.

If it is determined 910 that a rapid chat session is not desired, or after a rapid chat session has concluded, a determination 912 may be made as to whether reports are needed. If reports are needed, the provider user may obtain 913 system reports, performance metrics, or other forms of analysis. The provider user may obtain 913 these items through an analytics interface that provides reports and information about patient usage of the after-care service 120, trends related to re-admissions of patients, and performance metrics relating to improvements in one or more patient's conditions over time while using the after-care service 120.

Figure 10:
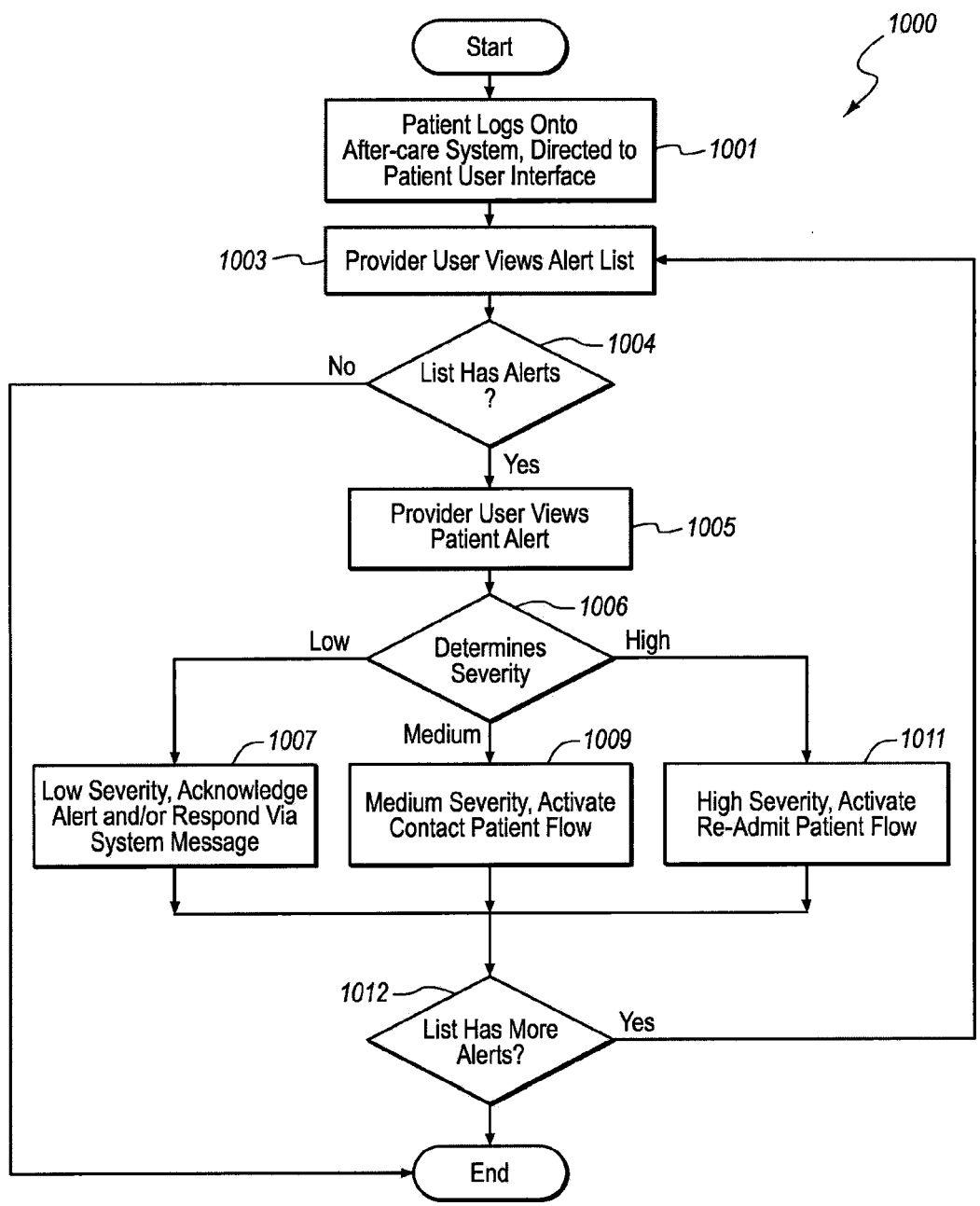
FIG. 10 is a flow chart illustrating one embodiment of a method for monitoring alerts related to the recovery program.

Certain embodiments of the present systems and methods may relate to a process for allowing a provider 113 to monitor alerts to improve the patient recovery process by ensuring that all patient problems are addressed and resolved. FIG. 10 is a flow chart illustrating one embodiment of a method 1000 for allowing the provider 113 to monitor alerts to improve the patient recovery process. In one embodiment, certain activities of various users 110 (e.g., a provider user of the provider 113) in relation to the after-care service 120 may be automated and performed by a computer application.

In one configuration, a designated provider user (e.g., a nurse, a doctor, an administrative personnel member, etc.) from the provider 113 logs into the after-care service 120. The provider representative may view 1003 an alert list that provides a summary of patients (e.g., a listing of names of patients, overall status, and summary of activities), and a summary of tasks associated with the patients. The tasks may represent any number of concerns. For example, the tasks may represent notifications regarding patient inactivity (e.g., a patient who fails to complete an activity in its entirety or in a timely manner). Alternatively, the tasks may represent notifications regarding patient problems (e.g., a patient who is unable to complete a scheduled activity). The tasks advantageously notify the provider 113 of small concerns before the concerns turn into big concerns that require readmission of the patient.

A determination 1004 may be made as to whether the alert list includes alerts/provider tasks that require further investigation. In one example, the provider user may review 1005 alerts associated with a particular patient 111. The provider user may also view information associated with that patient 111 (e.g., the scheduled activity at issue, including its description, scheduled time, special instructions, and completion status). Examples of a completion status may include "No Activity Reported" (the patient 111 did not enter specify whether he or she completed the activity); "Unable to Complete Activity" (the patient 111 specified that he or she was unable to complete the activity); "Activity Completed with Problems" (the patient 111 specified that he or she was able to complete the activity, but experienced problems, complications or issues in doing so); "Activity Completed without Problems" (the patient 111 specified that he or she was able to complete the activity without experiencing any difficulties, complications or problems).

Provider staff members may be able to view patients and tasks related to that staff member through a provider team structure association. The provider team structure may be a flexible team-based structure that allows for various staff members working in various roles to be associated with patients, procedure teams, and scopes of responsibility within each. Each provider team may be an abstract definition of a team to which the staff members are associated. Within each team, the associated staff members may perform one or more roles.

In one example, Doctor A is the surgeon for Procedure X. Doctor A may have a team of four nurses that handle the general monitoring and care for patients of the first doctor. Doctor A and the four nurses may be associated with a provider team. Within that team, Doctor A may work in the physician role (i.e., he or she is responsible for making medical decisions) and the four nurses may work in a supporting role (i.e., they are responsible for supporting the patients).

Each role may be defined to allow or disallow access to or responsibility for a type of provider task. This controls which members of which roles are responsible for the provider tasks related to the patients assigned to a provider team.

A provider portal within the after-care system 120 may include an administrative function for managing the provider team structure. This allows administrator users to define new provider teams, associate provider staff members with those teams and define, edit and customize the role relationships to specify the provider tasks accessible to each team or role.

The provider 113 may define its own set of rules for determining the severity of a completion status (i.e., no activity was reported, activity could not be completed, activity was completed with problems). As the provider user views each system task, the provider user reviews the task details to determine 1006 the severity of the reported status. In one embodiment, the task is determined 1007 to be of a low severity, and the provider user may acknowledge the task and specify that the task no longer requires review or a listing in the task list. For example, making the acknowledgement may be accomplished via clicking on an acknowledge button displayed on a screen of a computing device used by the provider user. When appropriate, the provider user may enter a message with an explanation relating to the task. For other types of tasks, the provider task system may provide the staff member with an interface to complete some form of data entry and action.

In one embodiment, the provider task system is a workflow system that manages the tasks and activities that staff members within the provider organization need to review, approve, or complete to support the use of the after-care system 120. The tasks for the provider task system may be generated by at least two methods: event-based generation and timer-based generation. Each type of provider task may define its own method for task generation, which may be a combination of both event-based and timer-based.

The provider tasks may be displayed to the members of the provider organization through a tasks section of a provider portal. The task section may display all of the tasks associated with the current provider user according to their relationship to the type of task and associated patient via the provider team structure. This flexible structure may allow the provider tasks to be worked by a team of people and may avoid tasks being assigned to unresponsive, unavailable, or non-working staff members.

In one embodiment, the provider staff member may view a list of tasks associated with their scope of responsibility. They will be able to click on any task to see the details of that task. A task detail display may show the provider staff member the history of that task including any notes that have been entered by other staff members that have accessed or worked on the task. The task detail display may also show the provider staff member the description of the task and the instructions for completing the task.

The task detail display may also include a task implementation window. The provider staff member may view the specific user interface elements to guide them toward completion of the provider task. For some provider tasks, this section may ask the provider staff member to enter some data into form fields to complete the task. For other types, this section may direct the staff member to complete some function in another system and click on some control that provides a digital signature confirming the external function was completed.

Once the provider staff member has completed the provider task, the task may be updated and marked as completed. This will cause it to no longer appear in the provider task list for that staff member or other staff members with a similar scope of responsibility. The following is one example of the types of provider tasks and an example of their intended purpose.

Patient Enrollment: This provider task may appear when a new patient record is identified such that the patient has an upcoming procedure and needs to be setup in the after-care system 120, begin their orientation with the system 120, and begin following the procedure preparation protocol. This task type may require the staff member to confirm the provider team that will be responsible for the patient and the preparation program that patient should follow prior to their procedure.

Patient Discharge: This provider task may appear when a current patient record is identified such that their procedure has been completed and their post-procedure, in-patient recovery is nearly complete. This task type may require the staff member to confirm the provider team that will be responsible for the patient and the recovery program that the patient should follow when they have returned to their home after being discharged. This task is typically generated through an electronic medical record (EMR) integration when an admissions discharge transfer (ADT) message is processed.

Patient Inactivity: This provider task may appear when a current patient record is identified such that the patient is not actively using the after-care system 120 or the patient's use of the system has become non-compliant. This task type may require the staff member to indicate that they have made an attempt to contact the patient at home to check on the status of the patient and if they need help with their recovery or their use of after-care system 120.

Patient Symptom Follow Up: This provider task may appear when a current patient record is identified such that the patient has reported one or more alarming responses to their daily symptom survey. This task type may require the staff member to indicate that they have reviewed the reported symptoms with the physician responsible for the reporting patient.

Patient Completion: This provider task may appear when a current patient record is identified such that the patient has completed their recovery program. This provider task serves as notification to the provider that the patient has successfully completed their recovery. For some providers, they may enter some provider-specific data to track the end of the recovery for that patient. In some other cases, the provider may indicate that they have completed some series of provider-specific steps in external provider systems to facilitate and track the completion of that patient's recovery.

Patient Message Requires Response: This provider task may appear when a current patient record is identified such that the patient has submitted a health chat message to the provider. This task type may require the provider staff member to read the submitted message and provide a response to the patient.

In one embodiment, the provider task/alert may be determined 1009 to be of a medium severity, and the provider representative may respond to the alert according to escalation procedures defined by the provider 113 for the particular type of activity and problem. For example, the provider representative might initiate a process flow that contacts the patient 111 for direct communication via the chat interface or to schedule the patient 111 for a phone call to discuss the reported problem.

In one configuration, the alert may be determined 1011 to be of high severity, and the provider representative responds to the alert according to escalation procedures defined by the provider 113 for the particular type of activity and problem.

For example, the provider representative might initiate a process flow that facilitates readmission of the patient 111 (e.g., via a chat session, a phone call, etc.)

After reviewing each task/alert for a patient 111, a determination 1012 may be made as to whether additional alerts exist. If there are additional tasks/alerts to review, the provider representative may begin to work the next task in the list. If there are no more additional tasks, the method 1000 may end.

Figure 11:
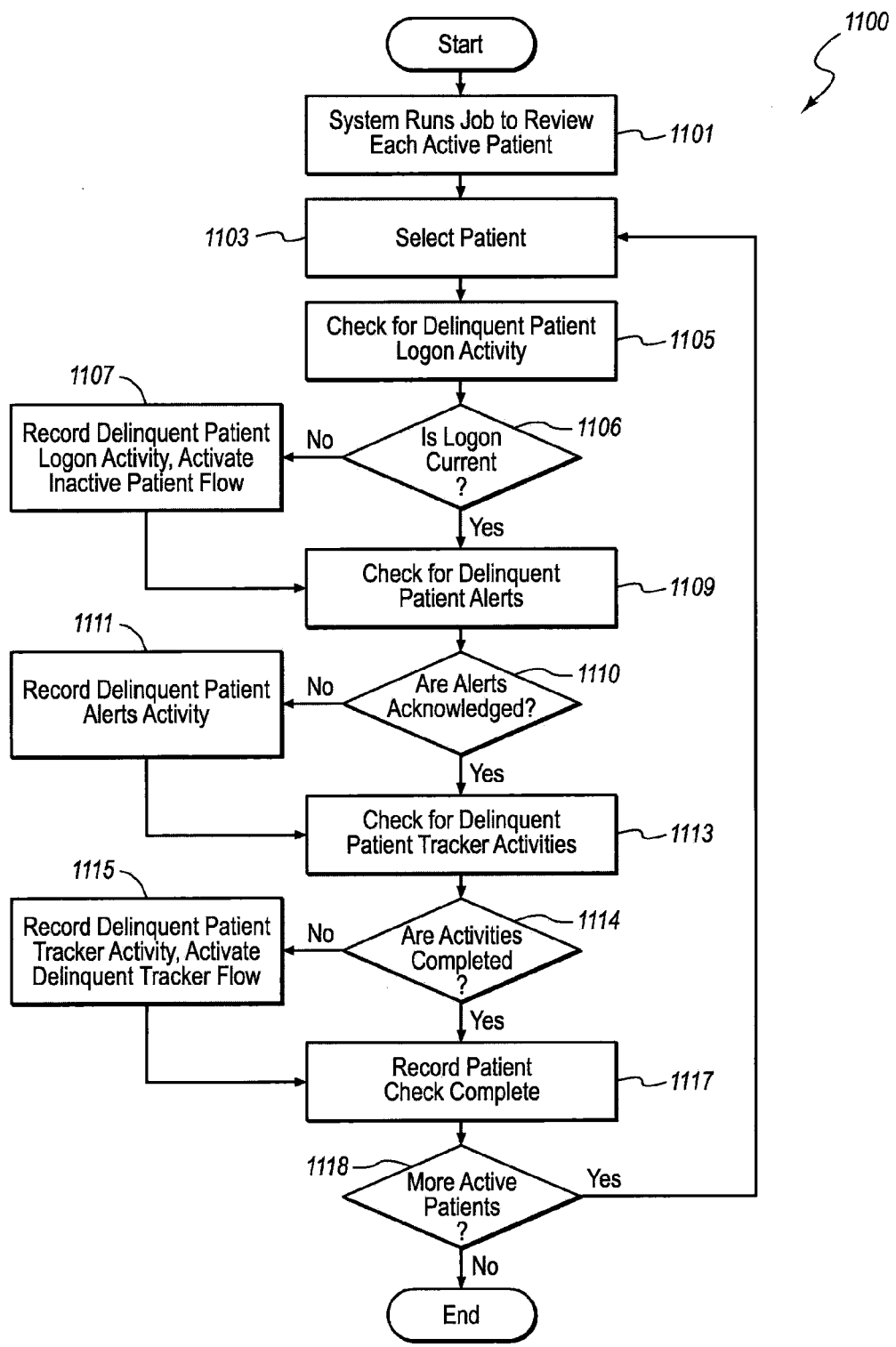
FIG. 11 is a flow chart illustrating one embodiment of a method for automatically auditing the user's tracking data.

FIG. 11 is a flow chart illustrating one embodiment of a method 1100 for automatically auditing the progress of selected patients.

In accordance with one aspect of the present systems and methods, the after-care service 120 may proactively review patient record data to identify problems related to activities and events patients are not satisfactorily completing (e.g., failure to log into the service, failure to record activity results, failure to complete an activity, failure to complete an activity without problems, and the like). The application server 121b may run a computer application to automatically audit one or more patients at a designated time. The application may run on a scheduled interval or upon a command from the system administrator 119 or service representative 129. The application may select 1103 a patient, and inspect that patient's record in the databases 125a, 125b, 125c for certain data (e.g., reported and unreported activities, other status information).

The application may check 1105 for delinquent patient logon activity. A determination 1106 may be made as to whether the patient 111 has logged into his or her account at predefined intervals. Delinquent log-in activity may be a measure of whether or not the patient is logging onto the system in a timely manner such that the frequency of and intervals between log-ins agree with the predefined timing requirements for each provider 113.

If it is determined 1106 that the logon activity is not current, the application may record 1107 a delinquent patient log-in warning in the databases 125a, 125b, 125c (e.g., in the patient's 111 record or a separate record dedicated to such warnings). The warning may be tracked by the after-care service 120, analyzed using predefined metrics, correlated with other data (e.g., the patient's 111 history of delinquency, historical data of multiple patients 111), and reported to a user 110 (e.g., the patient 111, the provider 113, the primary physician 115, the insurance provider 117). Depending on the rules defined by the provider 113, a delinquent patient log-in warning may initiate a separate workflow for a provider representative to address the issue.

If, however, it is determined 1106 that the logon activity is current, the application checks 1109 whether the patient 111 has failed to review or resolve a patient alert during a predefined timeframe specified by the provider 113. A determination 1110 may be made as to whether alerts have been acknowledged by the patient 111. If alerts have not been acknowledged, the application records 1111 a delinquent patient alert warning in the databases 125a, 125b, 125c (e.g., in the patient's 111 record or a separate record dedicated to such warnings). The warning may be tracked by the after-care service 120, analyzed using predefined metrics, correlated with other data (e.g., the patient's 111 history of delinquency, historical data of multiple patients 111), and reported to a user 110 (e.g., the patient 111, the provider 113, the primary physician 115, the insurance provider 117). Depending on the rules defined by the provider 113, a delinquent patient alert warning may initiate a separate workflow for a provider representative to address the issue.

If, however, it is determined 1110 that alerts have been acknowledged, the application may check 1113 whether the patient 111 has failed to record or complete a scheduled calendar activity with respect to predefined parameters. A determination 1114 may be made as to whether activities are completed. If it is determined 1114 that activities have not been completed, the application records 1115 a delinquent patient activity warning in the databases 125a, 125b, 125c (e.g., in the patient's 111 record or a separate record dedicated to such warnings). The warning may be tracked by the after-care service 120, analyzed using predefined metrics, correlated with other data (e.g., the patient's 111 history of delinquency, historical data of multiple patients 111), and reported to a user 110 (e.g., the patient 111, the provider 113, the primary physician 115, the insurance provider 117). Depending on the rules defined by the provider 113, a delinquent patient activity warning may initiate a separate workflow for a provider representative to address the issue.

If, however, it is determined 1114 that activities have been completed, the application may complete 1117 the audit of the particular patient 111. A determination 1118 may be made as to whether additional patients exist to audit. If there are additional patients to audit, the method 1100 may be repeated for each additional patient. Otherwise, the method 1100 may end.

Figure 12:
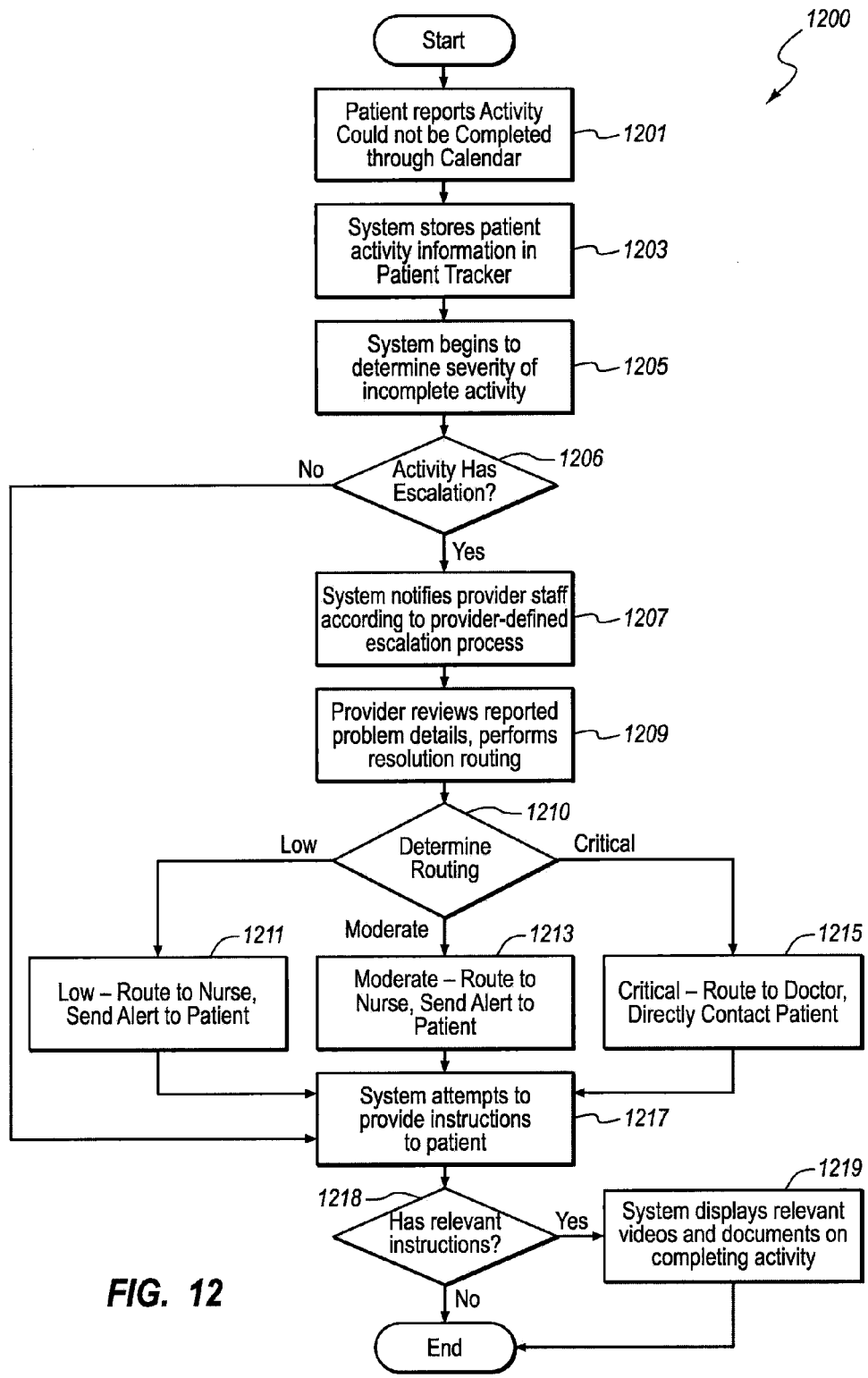
FIG. 12 is a flow chart illustrating one embodiment of a method for tracking the progress of the user, and reporting the progress to the provider.

FIG. 12 is a flow chart illustrating one embodiment of a method 1200 for tracking the progress of a patient 111, and reporting that progress to a provider 113.

In one embodiment, the patient 111 indicates the status for a particular calendar activity (e.g., not completed, completed with problems, complete without problems). For example, the patient 111 reports 1201 that the activity could not be completed. The patient 111 makes the indication in the calendar by clicking on a box labeled "could not be completed," selecting a description "could not be completed" from a drop down menu, or some other suitable method for indicating the status of the activity.

The after-care service 120 may store 1203 the indication in the databases 125a, 125b, 125c (e.g., in the patient's 111 record). The after-care service 120 may determine 1205 the severity of the status for the activity. For example, the after-care service 120 may compare the details of the activity and its status to escalation procedures defined by the provider 113. An escalation procedure is an issue resolution communication plan that details the sequence of people that receive a message following certain status indications for certain types of activities from certain patients. A determination 1206 may be made as to whether the activity has an escalation procedure. If the activity/status combination has no associated escalation procedure (as defined by the provider 113 for each type of treatment, recovery program, activity and patient) the after-care service 120 may send 1217 additional instructions to the patient 111, but may not send any messages to other users 110.

If, however, the activity/status combination is associated with an escalation procedure, a provider representative may be notified 1207 in accordance with the predefined escalation procedures designed by the provider 113. For example, the after-care service 120 may notify 1207 a provider representative who reviews some or all of the inbound notifications. Alternatively, the provider 113 may not designate a particular person to review all notifications. Under these circumstances, the after-care service 120 might directly notify a nurse or doctor.

The provider representative (or other medical professional) may diagnose 1209 the problem. For example, the provider representative might log into the after-care service 120 to review the patient's 111 file as described in FIG. 9 and FIG. 10. After reviewing the file, a determination 1210 may be made as to the appropriate response for the diagnosis (e.g., contact the patient 111, forward the problem to another medical professional, etc.).

Steps 1211-1215 of the method 1200 describe three examples of responses based on the activity/status combination. For example, the after-care service 120 or provider representative might notify a nurse via email, text message, or chat session when the activity/status combination is of low 1211 or moderate 1213 severity. Alternatively, the after-care service 120 or provider representative may notify a doctor via phone when the activity/status combination is of critical 1215 severity.

The after-care service 120 may attempt to provide 1217 instructions to the patient 111. This step, like all other steps in any process flow, may take place at a different time in the process flow 1200 in relation to other steps. For example, the after-care service 120 might attempt to provide instructions before contacting the provider representative. A determination 1218 may be made as to whether the patient 111 has relevant instructions. If the service 120 has relevant instructions for the patient, the after-care service 120 may display 1219 various instructions to the patient 111, including instructional materials that are stored in the databases 125*a*, 125*b*, 125*c* for a particular activity or treatment upon completing the activity. Alternatively, the instructions may be provided via weblinks to outside sources of information.

Figure 13:
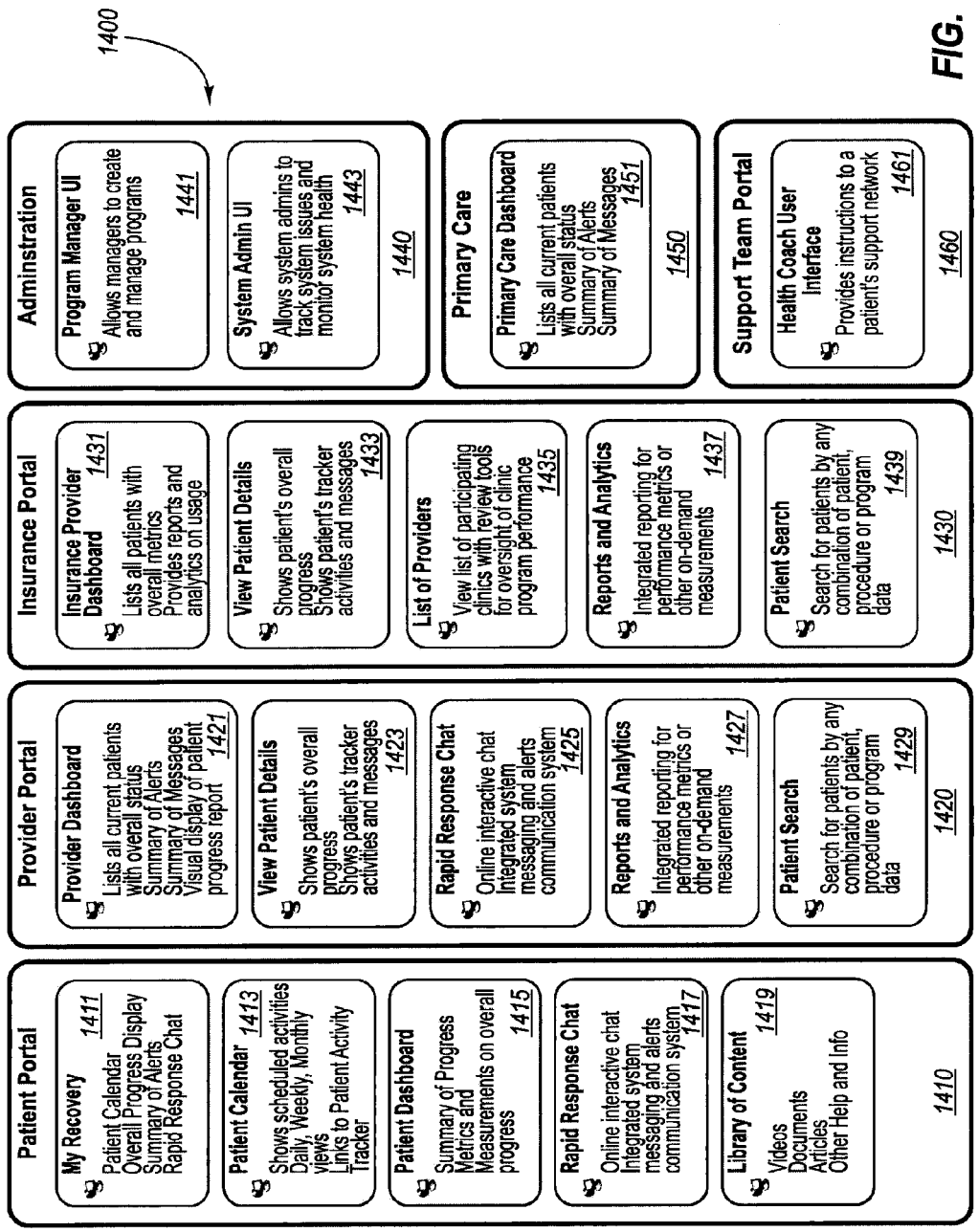
FIG. 13 illustrates one embodiment of a chart describing various user interfaces that are designed to interact with various users of the present systems and methods.

Additional embodiments of the present systems and methods may pertain to web-based interfaces of the after-care system 120 that interact with the various users 110. For example, FIG. 13 illustrates a chart 1400 describing various user interfaces that are designed to interact with the patients 111, the providers 113, the primary care physicians 115, the insurance providers 117, the administrators 119, and members of the support network 109.

In one example, the patients 111 interact with a patient portal 1410. The patient portal 1410 may include a MyRecovery patient "home" webpage ("page") 1411 displaying snapshots of the patient calendar, the patient's overall progress, the summary of alerts and messages, and the health chat interface. A patient calendar page 1413 shows, in greater detail, the calendar of activities and other tasks for the patient 111. The calendar view may assist the patient 111 to visualize what he or she needs to do and when each activity or task must be completed. The patient calendar page 1413 may provide the patient 111 with access to other pages or multimedia windows with instructions and details relating to each scheduled activity, and may also connect the patient 111 to a tracking display. A patient dashboard page 1415 may display to the patient 111 a summary of his or her overall progress through the program, which includes a summary evaluation of activity completion and service usage. A health chat page 1417 may provide the patient 111 with an interface to initiate and participate in interactive chat and offline messaging. An example may include a patient message board. The patient message board may be a messaging tool that allows patients and members of their support network to communicate using a common, shared forum. Messages from all members may be intermixed and sorted by the date the message was added. This may allow members of the support network to leave a helpful, inspirational message for the patient. This may also allow the patient (and other support members) to add their comments and reply through the addition of their own message board posts.

The patient message board may be accessible from a menu on the patient portal 1410. When the message board loads, it may show all of the recent messages for that patient's message board. When the user scrolls down through the list of messages and reaches the last message, the user may be presented with an option to load more messages. After clicking on this link, the system may load the remainder of the patient's message board messages. The user may also be presented with an option to add a new message to the message board. The user may type the text of their message in a text area. When the user finishes, he or she may click the submit button to post their message. The new message may appear at the top of the message board's list of messages and be visible to all members of the patient's support network and the patient himself or herself.

A patient program overview may also be available via the patient portal 1410. The overview may provide a summary of information about the patient's procedure, the recovery program, and the associated milestones, phases, risks, and symptoms related to the recovery program. When the patient program overview is accessed, the patient may see an overall timeline that represents the various phases of the procedure and recovery program. This may include pre-procedure preparation, in-patient stays for the procedure, in-patient stays for recovery, discharge, the phases of their at-home recovery, program completion, and any post-recovery maintenance phase or phases. A video may be accessible via the patient portal 1410 that explains each phase and detail of the procedure and recovery the patient is about to undergo. The timeline may give the patient an idea of what and when they will be doing various activities through the course of their procedure and recovery program. The patient may also be able to see a summary of the various categories of recovery activities related to their recovery program. Within each category summary, the patient may be able to read about the types of activities they will be directed to perform and the motivation, justification, and risk/reward related to performing the activities as prescribed. This may help the patient to understand what they are doing and how it will contribute to improving their recovery outcomes.

In one embodiment, a summary of the major risks related to the patient's recovery may also be available from the patient program overview. This may be an educational tool to help the patient understand the most common problems that occur that lead to readmission or continued illness. The overview may also summarize the major symptoms the patient and their support network should identify. This may educate the patient on the alarming conditions that can be detected by the patient or their network that, if addressed early, may help to reduce the risk of readmission or continued illness.

The patient 111 may also access specific details of their procedure through the patient portal 1410. This may be useful for the patient 111 should an emergency situation arise where the patient needs to seek medical treatment from a medical provider other than the provider that performed the procedure. The patient procedure details may include an operative note (Op Note) and a continuity of care document (CCD). The information included in the Op Note may detail the specifics of what happened during their procedure (such as if and how much anesthesia was used) as recorded by the medical staff performing the procedure. The information in the Op Note may also include a doctor's note, which may be a written detail from the doctor describing what he or she did, how the patient 111 responded, and any notes of interest for the procedure. The information in the Op Note may be received by the after-care system 120 via the EMR integration where the patient's information is pulled from the provider's systems at the time of discharge.

The patient portal 1410 may also include an educational and awareness tool for the patient 111 and his or her support network in the form of the patient symptom display. The display may show a summary of the major concerning symptoms according to the current phase of the patient's recovery. This may assist the patient and his or her support network to know and understand when certain high-risk symptoms are being shown so that they may notify a medical provider of potential issues before they become problems. The patient symptom display may include a data capture mechanism that allows patients to provide daily feedback on any of these potential symptoms. The feedback may be captured into the after-care system 120 and routed back to the medical provider through the use of various reports, provider tasks, and notification workflows. This information flow may allow the providers to see a summary of any reported symptoms for each patient while reviewing the patient's information.

The after-care system 120 may be capable of integrating with at-home monitoring devices that capture patient's vital readings. These devices may capture readings such as heart rate, blood pressure, and glucose levels. The system 120 may be able to retrieve the readings from these devices using standards-based and proprietary device APIs and push that data back to the after-care system 120 through proprietary APIs that capture patient vital readings into a patient symptom and data capture module.

In addition to the symptom display and data capture functionality described above, the after-care system 120 may provide a flexible and straightforward mechanism for patients to report a problem to the medical provider through a reporting functionality. When the patient 111 activates this functionality from the patient portal 1410, the patient may be prompted with a user interface to collect information relating to the problem being reported. The patient 111 may define the nature of the problem by selecting from a pre-defined set of problems (specific to their recovery) in a dropdown list. Once the patient has selected the problem, the patient 111 may be prompted with a symptom survey that asks the patient 111 to describe any symptoms they are experiencing (specific to their recovery) through a series of check box selections (one per pre-defined symptom). When the patient has finished filling out the survey, a summary notification may be generated and sent to the patient's support network. A provider task may also be generated and sent to the provider to notify them of the reported patient problem.

A health library page 1419 may be available to the patient 111 as a repository for content, instructions, and help. In one embodiment, the repository may be browsed and/or searched for particular content.

Providers 113 and provider representatives may interact with a provider portal 1420. The provider portal 1420 may include a provider dashboard 1421, which lists one or more patients, the overall status of patients, a summary of alerts, a summary of messages, and other information. A view patient details page 1423 may allow a provider representative to view the patient dashboard 1415 for a particular patient, which shows the provider representative the same summary information that the patient 111 can view. A health chat page 1425 may allow the provider representative to initiate or participate in interactive chat and offline messaging. A reports and analytics page 1427 may provide a provider representative with access to high-level reporting on program results for one or more patients at a time. The provider representative may view reports like re-admission rates and successful recovery program rates on a per-patient, per-treatment, per-provider, or other basis. A patient search page 1429 may allow a provider representative to search for specific patients using any combination of patient, treatment, or recovery program data.

The provider portal 1420 may facilitate the creation and editing of recovery programs. Based on the provider team structure, certain members within the provider organization may have access to a program builder module of the system 120. The after-care system 120 may present a set of available options to create a recovery program using dropdown menus along with the ability to define new options.

When defining a recovery program, the user starts by defining the recovery program name. The medical procedures related to the recovery program may then be defined from a list of procedures for that provider. This association may control whether or not this recovery program will be presented as an option when recovery programs are selected for patients at enrollment and discharge.

The recovery activities related to the program may be defined along with the schedule for each activity. This may be done by naming the activity and specifying the schedule (one-time, recurring, details of recurrence) for the activity. The user may also define the priority and/or significance of the activity, which may be used to provide a visual cue to the patient to indicate which tasks are more significant to their recovery than others.

After the activity has been defined, patient tracking options related to the activity can be defined. This may control what tracking options are shown to the patients when they are using the system 120. Included within the tracking options is the ability to display a variable survey to the patient when tracking their activity. This survey may display when the patient indicates that they were unable to complete an activity, when they were able to complete an activity or not at all. Each survey may be defined as a series of one or more questions. Each question may be defined with a textual question and a series of possible pre-defined answers. Questions may be defined such that they accept a free-form text response from the patients for situations where the pre-defined answers do not fully express the possible feedback from patients.

Once the activity has been defined, the content related to the activity may be defined. The content definition may include the textual descriptions for the activity, which consists of the textual instructions, the frequently asked questions (FAQs), the "Do's and Don'ts". The content definition also includes the association of any instructional videos that support the activity. Each activity may have zero, one or more videos associated with it. This process may then be repeated for each activity within the recovery program until all activities have been defined.

Once the program has been defined, it can be edited using the same interface. This interface consists of a list of defined recovery programs. Clicking on an item in the list will show the user the summary details of that individual recovery program. An "Activities" tab may list all of the activities related to the program. Clicking on an activity in the list may show the details of that activity, which includes the name, schedule, content and survey/tracking options.

A provider task system may be capable of functioning within the provider's current information technology (IT) systems without the use of the provider portal 1420. This may be useful in cases where doctors, nurses and clinicians do not want to use or cannot use another computer system interface within their practice. In these cases, the after-care system may deliver the details of patient-oriented tasks and notifications through the existing systems, interfaces, and tools that the provider staff members are already using.

For example, the first instance of this may be through an integration with the EMR system's task and workflow subsystem. Instead of delivering tasks into the provider task system that the after-care system 120 facilitates and displays through the provider portal 1420, the tasks may be generated and pushed to the EMR system so that the provider staff members can see, manage, and work on those tasks through their existing EMR software.

The second instance of this may be through email integration. In this case, all tasks may be distributed via the provider team structure to all of the associated provider staff members over email. Each email may include a summary of the task, the associated task instructions, and a summary of the patient information related to the task. This may allow provider staff members to continue to rely on their existing communication devices and systems to receive information related to the patients and their recovery efforts.

As previously explained, the after-care system 120 may be designed to integrate with EMR systems within a provider's IT configuration to automate the flow of patient information into the system 120. The foundation of this integration may be to capture the patient's primary identifying information and scheduled procedure information so that it may be reviewed and filtered to feed a patient enrollment process. This may also integrate the prescribed medications for the patient into the system 120 within a medications activity in the recovery activity list, described above. When a patient's medications are updated within the provider's EMR, the changes in medications may automatically synchronize with the recovery activity list.

In one embodiment, the after-care system 120 may be designed to be flexible and work with many types of EMR systems using industry standard HL7 interfacing APIs. The system 120 may use a data processing workflow to identify and import candidate patient and procedure records. Once imported, the provider may filter and select the candidate patients to feed the patient enrollment process. This may be either fully automated (using pre-defined filters) or partly automated and dependent upon manual review and selection. Once selected, the patient information may feed into the provider enrollment process where a provider task for patient enrollment may be created for each patient and their associated procedure information. The procedure information may include the Op Notes (what happened during the procedure along with the doctor's note, which describes what they did and how the patient responded) and the CCD.

The system 120 may also be capable of pushing sets of patient information collected through the patient's use of the system 120 back into the EMR system throughout or upon completion of the patient's recovery. The type of information may be defined by the provider, but may include detailed activity data or high-level summarized data.

Insurance providers 117 may interact with an insurance portal 1430. The insurance portal 1430 may include an insurance provider dashboard page 1431 that includes a list of providers 113, patients 111, and associated high-level reporting of analysis. A view patient details page 1433 may allow an insurance provider 117 to review the same details about a patient 111 and their recovery program activities that the patient 111 and provider 113 can review via the patient dashboard 1415. A list of providers page 1435 may provide a list of participating providers 113, and may be used to drill into additional details about particular providers 113, recovery program results, and specific patients 111 affiliated with certain recovery programs and/or providers 113. A reports and analytics page 1437 may offer insurance providers 117 access to system reporting based on configurable and customizable performance metrics. A patient search page 1439, much like the one in the provider portal user interface 1420, may allow insurance providers 117 to search for patients 111 using any combination of patient, treatment, or recovery program data.

System administrators 119 may interact with an administration portal 1440. The administration portal 1440 may include a system administration user interface 1443, which may allow system administrators 119 to monitor and manage the after-care system 120 activities and overall system health. The administration portal 1440 may also include an interface 1441 that allows administrators to setup and configure instances of the after-care system 120 for provider accounts.

Primary care physicians 115 may interact with a primary care portal 1450, which may include a primary care dashboard 1451 that allows primary care physicians 115 to view details about their patients. The primary care portal 1451 may be a web portal interface for primary care physicians. This interface may be designed to give primary care physicians and referring physicians visibility to each of their patients that are using the after-care system. The primary care portal 1451 may show the physician a list of their patients currently using the system 120. This list of patients may span multiple providers if they have patients using the system 120 through multiple, separate medical facilities that use the after-care system 120 to help their patients manage their recoveries. From this list, the physician may see the name, procedure, procedure date, provider name, and overall status of their patients. Clicking on one of the patient records may allow the physician to view the details of that individual patient. From this detail screen, the physician may see the patient's recovery activity calendar, the summary of their tracking activities, the summary of their symptom tracking, their message board, and the summary metrics for their usage.

In one embodiment, members of the support network 109 may interact with a support team portal 1460, which may include a health coach user interface 1461 that may be a web portal interface that provides tasks and instructions to the people that are supporting a patient during the recovery program. The patient portal 1410 may be designed to instruct the patient (or those helping them) how and when to perform their recovery activities. The health coach user interface 1461 may be designed to instruct the supporters how and when to perform their tasks to support the patient.

An activity list and calendar within the health coach user interface 1461 may be a task and calendar based interface that illustrates to a "health coach" what they need to do to support the patient. These supporting activities may start prior to the patient's procedure (preparation) and continue through the patient's recovery.

During preparation the health coach user interface 1461 may provide guidance to the health coach to help them prepare for their patient's procedure. This may include educating the coach on the types of supplies that will be needed at-home after the patient has been discharged and guidance on methods to procure those supplies. This may also include scheduling for dropping off the patient prior to their procedure and picking them up after they have been discharged as well as other tasks.

During recovery, the health coach user interface 1461 may provide guidance to the health coach to help them support their patient through the at-home phase. This may include utilities to prepare shopping lists for trips to the pharmacy for both medications (including the prescriptions from the provider) and supplies (bandages, solutions, creams). This may also include the activities that the health coach needs to complete to proactively ensure that the patient is keeping up with their recovery program and remaining compliant.

In one embodiment, the health coach user interface 1461 may work with the patient support network 109 to create and facilitate the notion of layered responsibility coverage across multiple support network members. Through this coverage, multiple support network members may provide coverage for blocks of time for the patient such that a first support member covers Monday, Wednesday, and Friday while a second support member covers Tuesday, Thursday, and the weekend. This coverage may also be defined with a backup support member so that a backup can be notified and made the primary care health coach when the original primary becomes unavailable.

The health coach user interface may 1461 also provide instructional materials (FAQs, Do's and Dont's, Videos, etc.) that provide training for the health coach to properly support the patient. These instructions may include general items such as cardiopulmonary resuscitation (CPR) and items specific to the recovery program such as "how to bathe" and "how to bandage".

In one embodiment, members of the patient's support network may receive email summary notifications. These notifications may be configured to be sent multiple times per day, once a day, once a week, etc. Support members may also choose how they would like to receive the notifications (text message, email, automated phone call messages). This gives the support member control over how often they would like to be notified.

The summary notifications may include summarized details about the patient's performance and activities within their recovery program. These details may include summaries of all completed activities, summaries of all missed activities, and summaries of all failed activities. These details may also include summaries of all access to the after-care system 120 (patient X logged in 3 times in the summary period or patient Y has not logged in during the summary period). These details may also include a summary of any reported symptoms and a summary of communications from the provider to the patient. Support members may elect to participate and receive these notifications (or elect not to participate) through the patient portal 1410.

Figure 14:
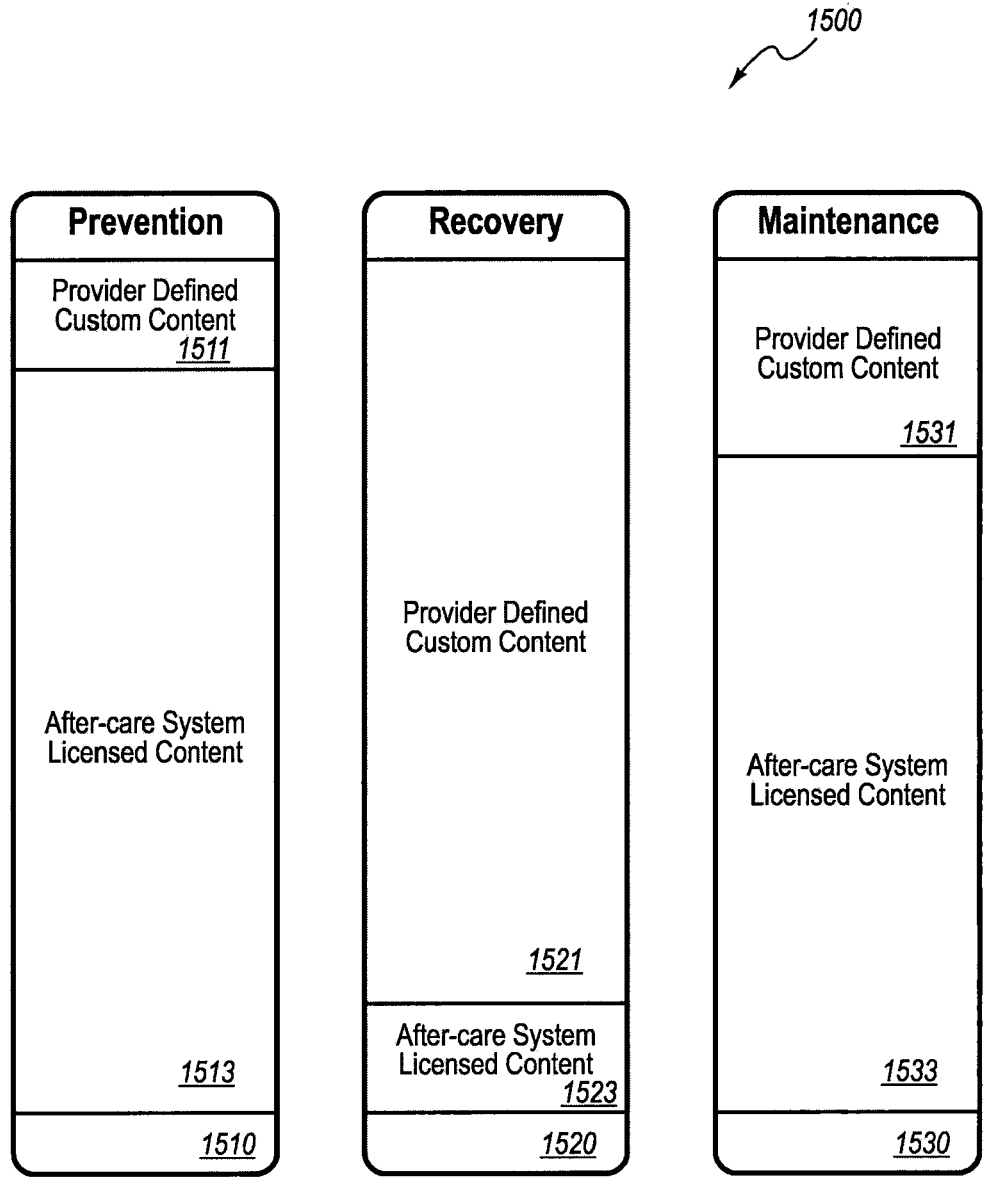
FIG. 14 illustrates one embodiment of a chart describing the development of certain data prior to generating the recovery program.

Additional embodiments of the present system and methods may pertain to developing the content offering of the after-care service 120. For example, FIG. 14 illustrates a chart 1500 describing how certain content is developed prior to generating after-care services for a particular treatment. As shown, a prevention service 1510 may be partially customized by content 1511 from a provider 113, but may be mostly based on content 1513 licensed by the after-care service 120 without input from the provider 113 (e.g., from outside sources, past recovery programs, analytics data). A recovery service 1520 and maintenance service 1530 may each include a different ratio of provider content 1521, 1531, respectively, and after-care licensed content 1523, 1533, respectively, to that of the prevention service 1510. The embodiments described above in relation to the recovery service 1520 may also be applicable to the prevention service 1510 and the maintenance service 1530.

Figure 15:
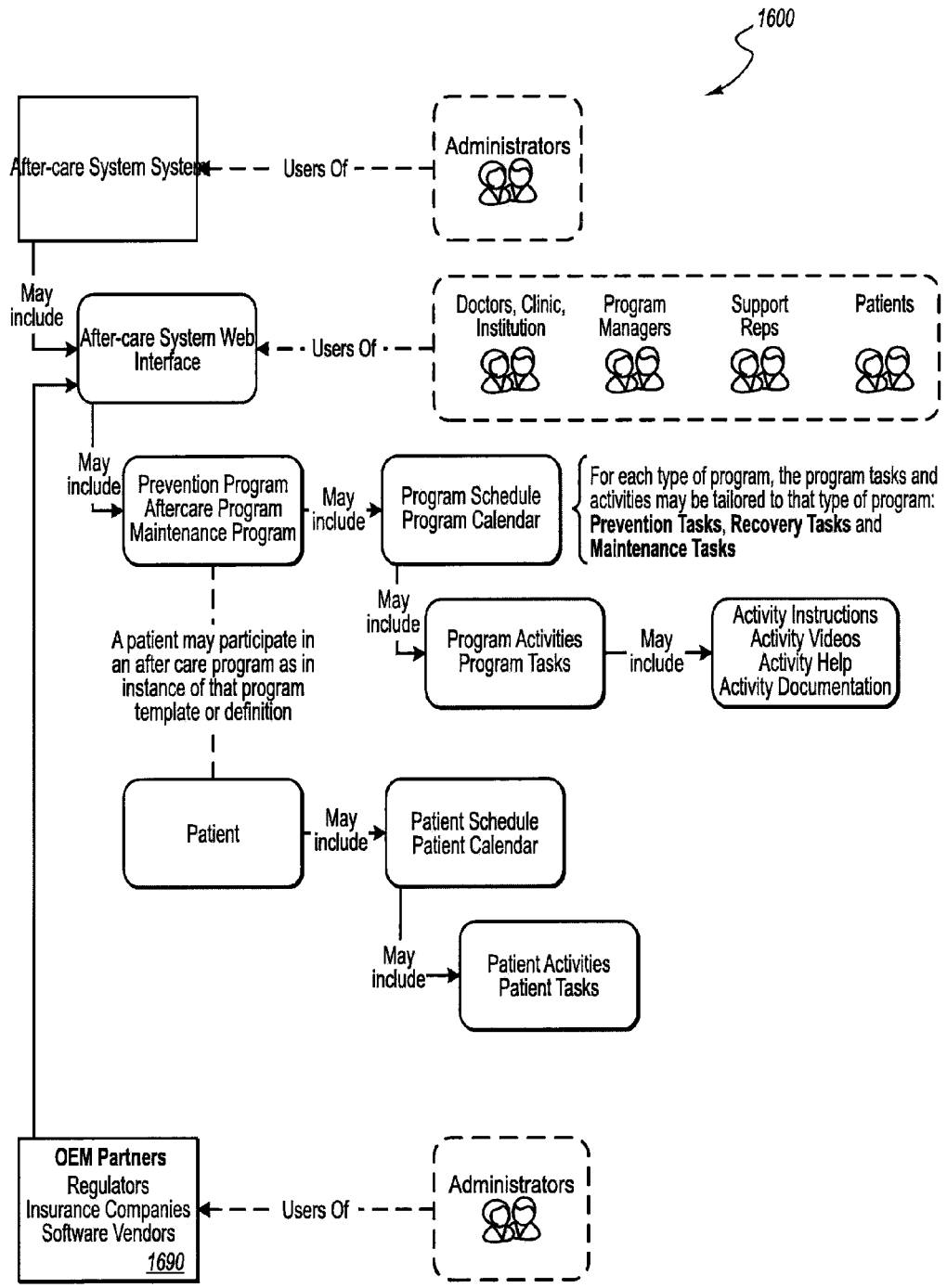
FIG. 15 illustrates one embodiment of a chart describing relationships between various users of the present systems and methods.

Additional embodiments of the present system and methods may pertain to original equipment manufacture (OEM) partnerships where another company sells and/or manages the after-care system 120 and/or service under its own name and/or branding. For example, FIG. 15 illustrates a chart 1600 describing how an OEM partnership might take place in accordance with the present systems and methods. As shown, an OEM Partner 1690 may take on the sales and customer service responsibilities while utilizing the after-care system 120 to support the overall operation of the OEM's product. In certain circumstances, different providers 113 may be associated with different OEM partners 1690. A particular OEM partner 1690 may have administrative oversight for its set of providers 113, in addition to all patients, and data that fall underneath that set of providers 113.

Figure 16:
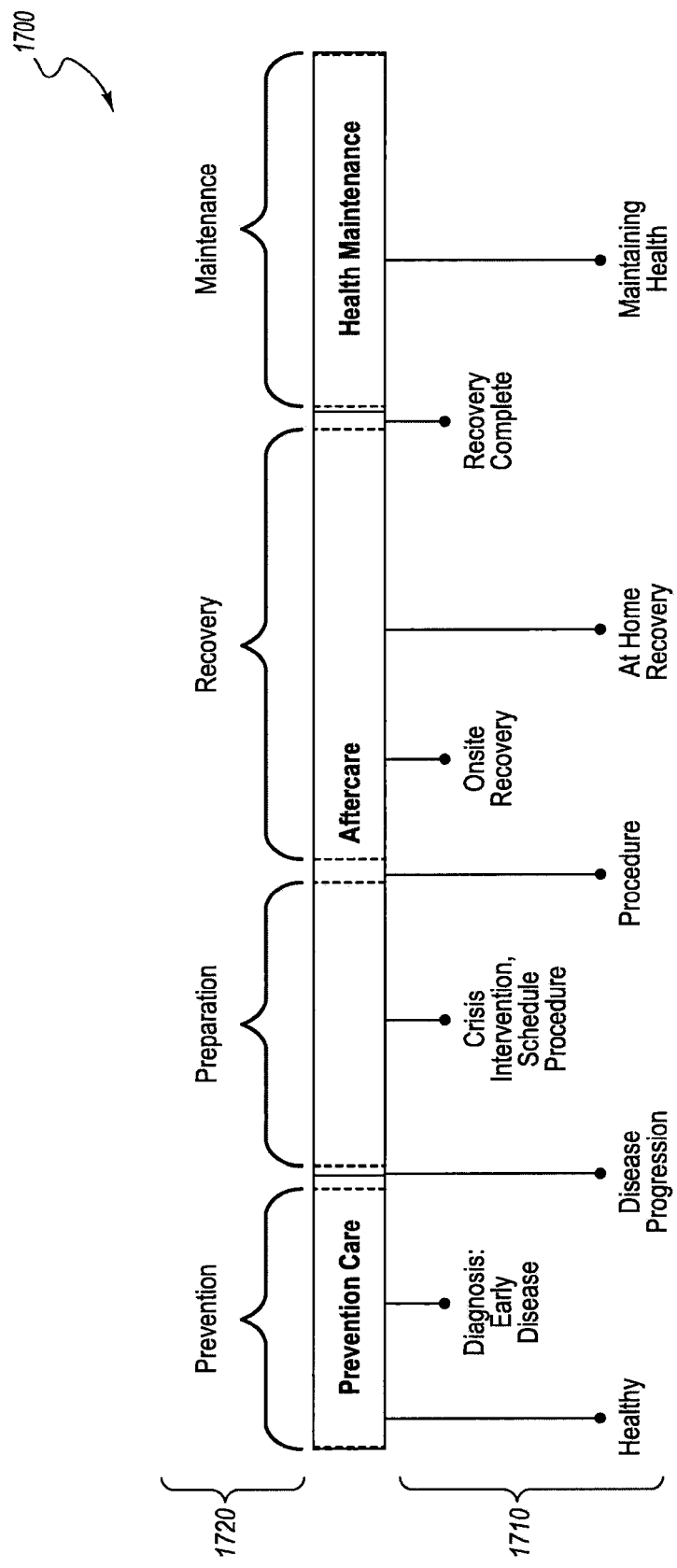
FIG. 16 illustrates one embodiment of a sequence of events and associated services in accordance with the present systems and methods.

Additional embodiments of the present systems and methods may pertain to a sequence of events that control which after-care service is provided to a user 110. For example, FIG. 16 illustrates a sequence of events 1710 (e.g., diagnosis, schedule procedure, at home recovery, maintaining health), and associated services 1720 (e.g., prevention, preparation, recovery, maintenance).

In one configuration, the after-care system 120 may capture detailed information on patient's recoveries and the impact that good or poor usage by the patients can have on the patient's recovery. The system 120 may use this information for the betterment of their recovery programs as well as for showing how the system 120 positively impacts unplanned hospital readmission by a certain percentage. These reports may also show how the system 120 improves patient outcomes, reduces recovery times, and creates efficiencies for both provider and patient support networks to track and monitor patient recoveries.

Figure 17:
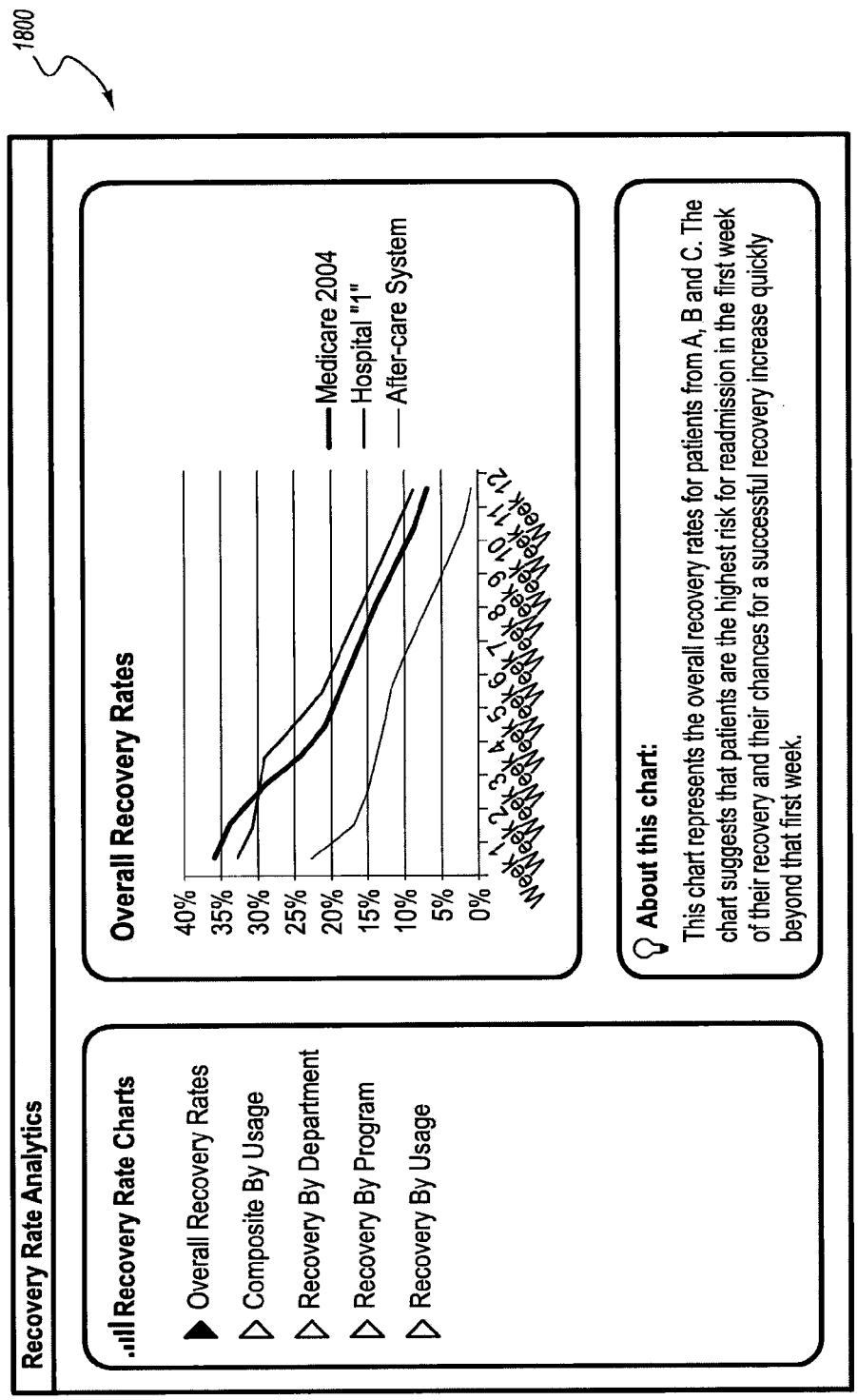
FIG. 17 illustrates one embodiment of a report that includes some of the metrics captured by an after-care system in accordance with the present systems and methods.

FIG. 17 illustrates one embodiment of a report 1800 that includes some of the metrics captured by the system 120. In one embodiment, the report may show the aggregate recovery outcomes week by week over the course of all patient recoveries as a line chart. The Y axis shows the successful recovery rate and the X axis shows the weeks (1-N) of that type of recovery program. The report shows multiple lines plotted. One line illustrates the Medicare average, which depicts the recovery rates for a blended group of Medicare patients for that type of procedure. The second line illustrates the recovery rates for patients that use the after-care 120 in accordance with the present systems and methods, but do so with what is considered poor usage. The third line illustrates the recovery rates for patients that use the after-care system 120 in accordance with the present systems and methods and do so with what is considered to by good usage. The report 1800 shows that the critical time in a patient's recovery is the first X weeks of their recovery (where X varies between 1 and 3 depending on the type of procedure) and that both poor and good usage of the after-care system 120 may impact recovery rates in both the first X weeks along with the remaining weeks.

Figure 18:
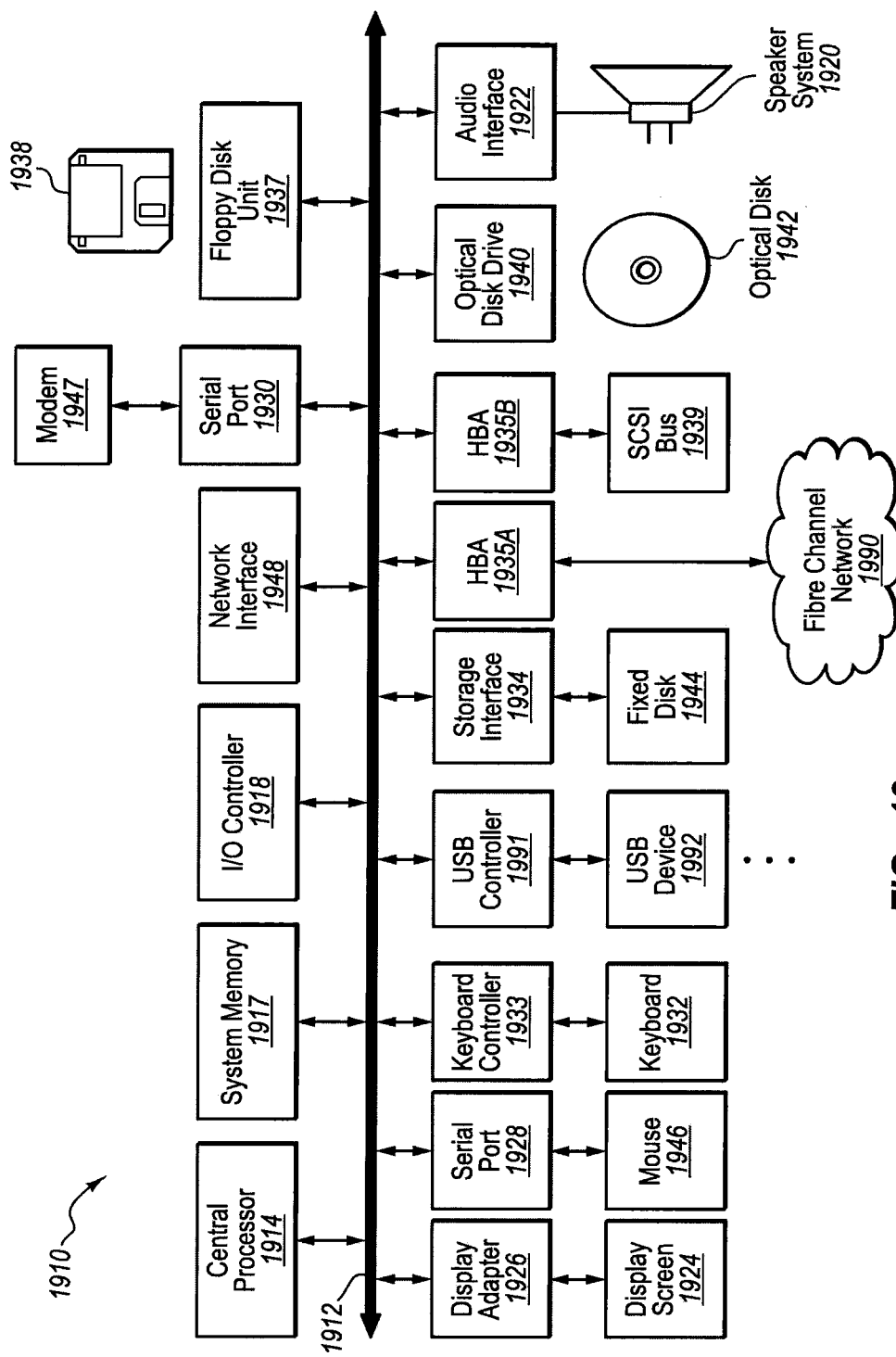
FIG. 18 depicts a block diagram of a computer system suitable for implementing the present systems and methods.

FIG. 18 depicts a block diagram of a computer system 1910 suitable for implementing the present systems and methods. Computer system 1910 includes a bus 1912 which interconnects major subsystems of computer system 1910, such as a central processor 1914, a system memory 1917 (typically RAM, but which may also include ROM, flash RAM, or the like), an input/output controller 1918, an external audio device, such as a speaker system 1920 via an audio output interface 1922, an external device, such as a display screen 1924 via display adapter 1926, serial ports 1928 and 1930, a keyboard 1932 (interfaced with a keyboard controller 1933), multiple USB devices 1992 (interfaced with a USB controller 1990), a storage interface 1934, a floppy disk drive 1937 operative to receive a floppy disk 1938, a host bus adapter (HBA) interface card 1935A operative to connect with a Fibre Channel network 1990, a host bus adapter (HBA) interface card 1935B operative to connect to a SCSI bus 1939, and an optical disk drive 1940 operative to receive an optical disk 1942. Also included are a mouse 1946 (or other point-and-click device, coupled to bus 1912 via serial port 1928), a modem 1947 (coupled to bus 1912 via serial port 1930), and a network interface 1948 (coupled directly to bus 1912).

Bus 1912 allows data communication between central processor 1914 and system memory 1917, which may include read-only memory (ROM) or flash memory (neither shown), and random access memory (RAM) (not shown), as previously noted. The RAM is generally the main memory into which the operating system and application programs are loaded. The ROM or flash memory can contain, among other code, the Basic Input-Output system (BIOS) which controls basic hardware operation such as the interaction with peripheral components or devices. Applications resident with computer system 1910 are generally stored on and accessed via a computer readable medium, such as a hard disk drive (e.g., fixed disk 1944), an optical drive (e.g., optical drive 1940), a floppy disk unit 1937, or other storage medium. Additionally, applications can be in the form of electronic signals modulated in accordance with the application and data communication technology when accessed via network modem 1947 or interface 1948.

Storage interface 1934, as with the other storage interfaces of computer system 1910, can connect to a standard computer readable medium for storage and/or retrieval of information, such as a fixed disk drive 1944. Fixed disk drive 1944 may be a part of computer system 1910 or may be separate and accessed through other interface systems. Modem 1947 may provide a direct connection to a remote server via a telephone link or to the Internet via an internet service provider (ISP). Network interface 1948 may provide a direct connection to a remote server via a direct network link to the Internet via a POP (point of presence). Network interface 1948 may provide such connection using wireless techniques, including digital cellular telephone connection, Cellular Digital Packet Data (CDPD) connection, digital satellite data connection or the like.

Many other devices or subsystems (not shown) may be connected in a similar manner (e.g., document scanners, digital cameras and so on). Conversely, all of the devices shown in FIG. 18 need not be present to practice the present systems and methods. The devices and subsystems can be interconnected in different ways from that shown in FIG. 18. The operation of a computer system such as that shown in FIG. 18 is readily known in the art and is not discussed in detail in this application. Code to implement the present disclosure can be stored in computer-readable medium such as one or more of system memory 1917, fixed disk 1944, optical disk 1942, or floppy disk 1938. The operating system provided on computer system 1910 may be MS-DOS®, MS-WINDOWS®, OS/2®, UNIX®, Linux®, or another known operating system.

Moreover, regarding the signals described herein, those skilled in the art will recognize that a signal can be directly transmitted from a first block to a second block, or a signal can be modified (e.g., amplified, attenuated, delayed, latched, buffered, inverted, filtered, or otherwise modified) between the blocks. Although the signals of the above described embodiment are characterized as transmitted from one block to the next, other embodiments of the present systems and methods may include modified signals in place of such directly transmitted signals as long as the informational and/or functional aspect of the signal is transmitted between blocks. To some extent, a signal input at a second block can be conceptualized as a second signal derived from a first signal output from a first block due to physical limitations of the circuitry involved (e.g., there will inevitably be some attenuation and delay). Therefore, as used herein, a second signal derived from a first signal includes the first signal or any modifications to the first signal, whether due to circuit limitations or due to passage through other circuit elements which do not change the informational and/or final functional aspect of the first signal.

Figure 19:
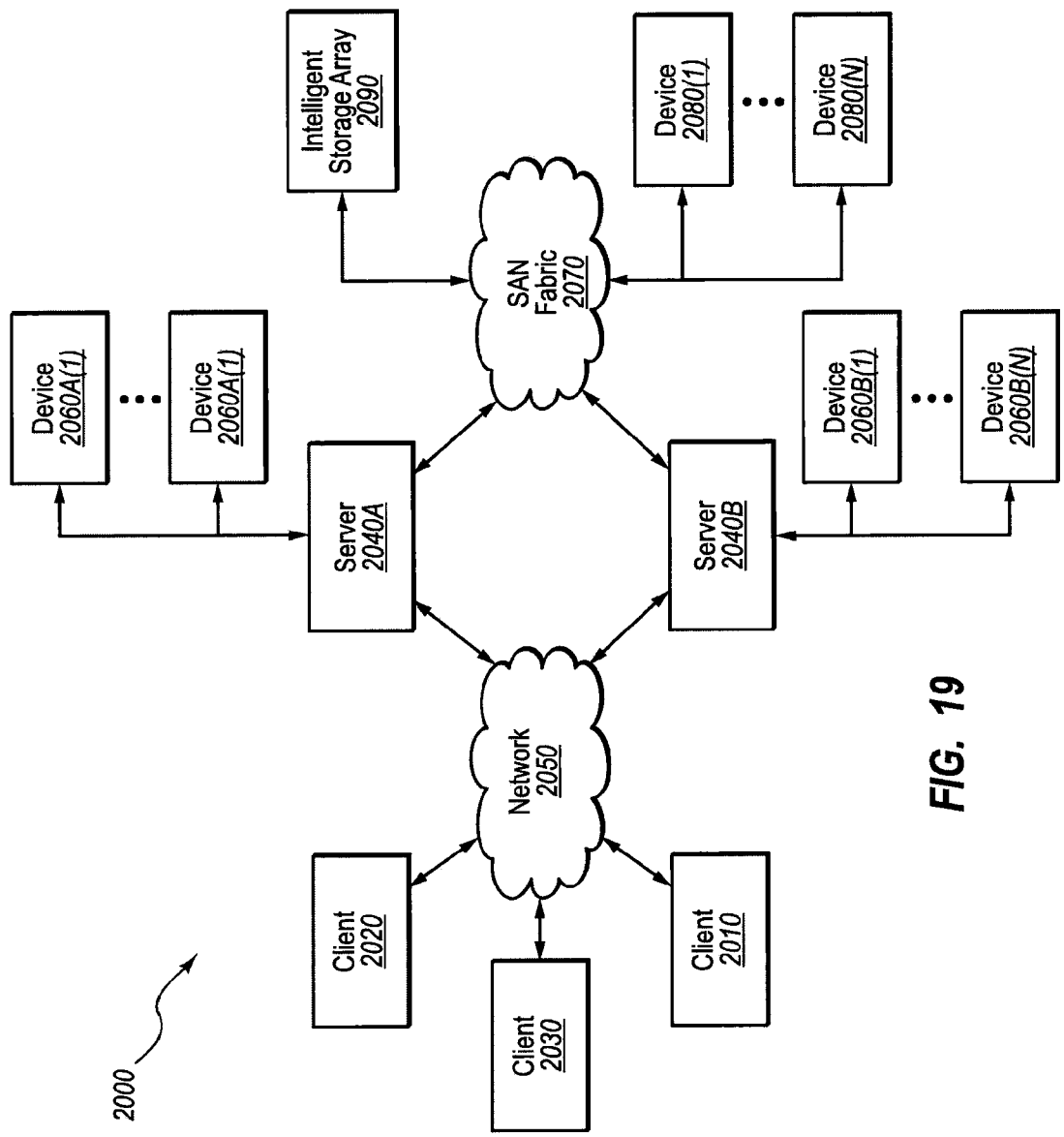
FIG. 19 is a block diagram depicting a network architecture in which client systems, as well as storage servers (any of which can be implemented using computer system), are coupled to a network.

FIG. 19 is a block diagram depicting a network architecture 2000 in which client systems 2010, 2020 and 2030, as well as storage servers 2040A and 2040B (any of which can be implemented using computer system 1910), are coupled to a network 2050. The storage server 2040A is further depicted as having storage devices 2060A(1)-(N) directly attached, and storage server 2040B is depicted with storage devices 2060B(1)-(N) directly attached. SAN fabric 2070 supports access to storage devices 2080(1)-(N) by storage servers 2040A and 2040B, and so by client systems 2010, 2020 and 2030 via network 2050. Intelligent storage array 2090 is also shown as an example of a specific storage device accessible via SAN fabric 2070.

With reference to computer system 1910, modem 1947, network interface 1948 or some other method can be used to provide connectivity from each of client computer systems 2010, 2020, and 2030 to network 2050. Client systems 2010, 2020, and 2030 are able to access information on storage server 2040A or 2040B using, for example, a web browser or other client software (not shown). Such a client allows client systems 2010, 2020, and 2030 to access data hosted by storage server 2040A or 2040B or one of storage devices 2060A(1)-(N), 2060B(1)-(N), 2080(1)-(N) or intelligent storage array 2090. FIG. 19 depicts the use of a network such as the Internet for exchanging data, but the present systems and methods are not limited to the Internet or any particular network-based environment.

While the foregoing disclosure sets forth various embodiments using specific block diagrams, flowcharts, and examples, each block diagram component, flowchart step, operation, and/or component described and/or illustrated herein may be implemented, individually and/or collectively, using a wide range of hardware, software, or firmware (or any combination thereof) configurations. In addition, any disclosure of components contained within other components should be considered exemplary in nature since many other architectures can be implemented to achieve the same functionality.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

Furthermore, while various embodiments have been described and/or illustrated herein in the context of fully functional computing systems, one or more of these exemplary embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the exemplary embodiments disclosed herein.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the present systems and methods and their practical applications, to thereby enable others skilled in the art to best utilize the present systems and methods and various embodiments with various modifications as may be suited to the particular use contemplated.

Unless otherwise noted, the terms "a" or "an," as used in the specification and claims, are to be construed as meaning "at least one of." In addition, for ease of use, the words "including" and "having," as used in the specification and claims, are interchangeable with and have the same meaning as the word "comprising."

What is claimed is:

1. A web-based method implemented by at least one computing device for automating a medical treatment plan, comprising:
   digitizing content related to a program that is associated with a medical treatment;
   storing the digitized content in a database;
   providing the digitized content to a patient via a user interface to assist the patient who is associated with the medical treatment;
   collecting data relating to the patient's progress with the program;
   analyzing the collected data;
   determining, using one or more computing devices, whether the collected data indicates that an activity specified by the digitized content has or has not been properly completed;
   determining, using the one or more computing devices, a completion status relating to the activity when the collected data indicates that the activity has not been properly completed;
   determining, using the one or more computing devices, whether an escalation procedure is associated with the completion status;
   identifying additional content relating to the activity when no escalation procedure is associated with the completion status;
   sending the additional content in response to determining that no escalation procedure is associated with the completion status; and
   executing the escalation procedure when the escalation procedure is associated with the completion status of the activity.

2. The method of claim 1, wherein the collected data includes an indication that a problem occurred in relation to completing an activity specified by the identified content, the method further comprising:
   comparing the indication and a predefined importance of the activity to an escalation procedure; and
   determining, based on the comparison, a sequence of recipients for one or more messages relating to the indication and the activity.

3. The method of claim 1, the method further comprising:
   determining a severity level associated with the completion status when the escalation procedure is associated with the completion status of the activity;
   receiving an acknowledgement of the completion status after determining that the severity level is a first severity level; and
   receiving a message intended for the patient after determining that the severity level is a second severity level.

4. The method of claim 1, wherein the identified content related to the program comprises an activity for the patient to complete, the method further comprising:
   receiving a status update relating to the patient's progress to complete the activity; and
   updating a patient record associated with the patient in response to the status update.

5. The method of claim 4, further comprising providing a notification to a provider of the medical treatment relating to the updated patient record.

6. The method of claim 4, the method further comprising:
   analyzing the status; and
   providing, to the patient, customized instructions in response to the status.

7. The method of claim 4, the method further comprising:
   displaying tracking metrics that detail the progress of the patient in relation to completing or not completing assigned activities based on the updated patient record.

8. The method of claim 1, wherein the completion status is selected from a group of completion statuses comprising a first completion status indicating that the activity was not completed, and a second completion status indicating that the activity was completed with problems.

9. The method of claim 1, wherein the completion status is selected from a group of completion statuses comprising a first completion status indicating that logon activity is not current, a second completion status indicating that the patient has not reviewed or resolved an alert, and a third completion status indicating that the patient has not recorded or completed the activity.

10. The method of claim 1, further comprising providing the results of the analysis to a third party associated with the medical treatment.

11. The method of claim 10, wherein the third party comprises a provider of the medical treatment, a physician that performs the medical treatment, or an insurance provider associated with the patient.

12. The method of claim 1 wherein the analyzing the collected data comprises:
    determining, based on historical data relating to a plurality of users, recovery outcomes related to the program over a first time period.

13. The method of claim 1, wherein the collected data includes data from one or more monitoring devices configured to capture the user's vital readings, including at least one vital reading selected from the group consisting of a heart rate, a blood pressure and a glucose level.

14. The method of claim 1, further comprising automatically generating the program for the patient based on a unique result of the medical treatment.

15. The method of claim 1, wherein the analyzing the collected data comprises:
    determining, based on historical data relating to a plurality of users, re-admission rates and successful recovery rates on a per-treatment basis.

16. A computing device configured to provide access to a web-based application to automate a medical treatment plan, comprising:
    a processor;
    memory in electronic communication with the processor;
    the web-based application configured to:
       digitize content related to a program that is associated with a medical treatment;
       store the digitized content in a database;
       provide the digitized content to a patient via a user interface to assist the patient who is associated with the medical treatment;
       collect data relating to the patient's progress with the program;
       analyze the collected data;

update a patient record associated with the patient in response to a status update relating to an activity of the program;

determine whether the collected data indicates that an activity specified by the digitized content has or has not been properly completed;

determine a completion status relating to the activity when the collected data indicates that the activity has not been properly completed;

determine whether an escalation procedure is associated with the completion status;

identify additional content relating to the activity when no escalation procedure is associated with the completion status;

send the additional content in response to determining that no escalation procedure is associated with the completion status; and execute the escalation procedure when the escalation procedure is associated with the completion status of the activity.

17. The computing device of claim 16, wherein the collected data includes an indication that a problem occurred in relation to completing an activity specified by the identified content, wherein the web-based application is further configured to:

compare the indication and a predefined importance of the activity to an escalation procedure; and determine, based on the comparison, a sequence of recipients for one or more messages relating to the indication and the activity.

18. The computing device of claim 16, wherein the web-based application is further configured to:

determine a severity level associated with the completion status when the escalation procedure is associated with the completion status of the activity;

receive an acknowledgement of the completion status after determining that the severity level is a first severity level; and receive a message intended for the patient after determining that the severity level is a second severity level.

19. The computing device of claim 16, wherein the web-based application is further configured to:

analyze the status; and provide, to the patient, customized instructions in response to the status.

20. The computing device of claim 16, wherein the web-based application is further configured to provide a notification to a provider of the medical treatment relating to the updated patient record.

21. The computing device of claim 16, wherein the completion status is selected from a group of completion statuses comprising a first completion status indicating that the activity was not completed, and a second completion status indicating that the activity was completed with problems.

22. The computing device of claim 16, wherein the completion status is selected from a group of completion statuses comprising a first completion status indicating that logon activity is not current, a second completion status indicating that the patient has not reviewed or resolved an alert, and a third completion status indicating that the patient has not recorded or completed the activity.

23. The computing device of claim 16, wherein the web-based application is further configured to provide the results of the analysis to a third party associated with the medical treatment.

24. The computing device of claim 23, wherein the third party comprises a provider of the medical treatment, a physician that performs the medical treatment, or an insurance provider associated with the patient.

25. The computing device of claim 16, wherein the web-based application is further configured to:

display tracking metrics that detail the progress of the patient in relation to completing or not completing assigned activities based on the updated patient record.

26. The computing device of claim 16, wherein the web-based application is further configured to:

determine, based on historical data relating to a plurality of users, re-admission rates and successful recovery rates on a per-treatment basis.

27. The computing device of claim 16, wherein the web-based application is further configured to:

determine, based on historical data relating to a plurality of users, recovery outcomes related to the program over a first time period.

28. The computing device of claim 16, wherein the collected data includes data from one or more monitoring devices configured to capture the user's vital readings, including at least one vital reading selected from the group consisting of a heart rate, a blood pressure and a glucose level.

29. The computing device of claim 16, wherein the web-based application is further configured to automatically generate the program for the patient based on a unique result of the medical treatment.

30. The computing device of claim 16, wherein the web-based application is further configured to:

provide at least one patient support network tool, wherein the tool provides information to a member of the patent support network to prepare the member to assist the patient to engage the program; and provide a notification to a patient support network of the patient in real time relating to the medical treatment and the program of the patient.

31. A computer-program product for automating a medical treatment plan, the computer-program product comprising a non-transitory computer-readable medium having instructions thereon, the instructions comprising:

code programmed to digitize content related to a program that is associated with a medical treatment;

code programmed to store the digitized content in a database;

code programmed to provide the digitized content to a patient via a user interface to assist the patient who is associated with the medical treatment, wherein the identified content related to the program comprises an activity for the patient to complete;

code programmed to receive a status update relating to the patient's progress to complete the activity;

code programmed to update a patient record associated with the patient in response to the status update;

code programmed to determine whether the collected data indicates that an activity specified by the digitized content has or has not been properly completed;

code programmed to determine a completion status relating to the activity when the collected data indicates that the activity has not been properly completed;

code programmed to determine whether an escalation procedure is associated with the completion status;

code programmed to identify additional content relating to the activity when no escalation procedure is associated with the completion status;

code programmed to send the additional content in response to determining that no escalation procedure is associated with the completion status; and code programmed to execute the escalation procedure when the escalation procedure is associated with the completion status of the activity.

32. The computer-program product of claim 31, wherein the instructions further comprise code programmed to:

collect data, including an indication that a problem occurred in relation to completing the activity specified by the identified content;

compare the indication and a predefined importance of the activity to an escalation procedure; and determine, based on the comparison, a sequence of recipients for one or more messages relating to the indication and the activity.

33. The computer-program product of claim 31, wherein the instructions further comprise code programmed to:

determine a severity level associated with the completion status when the escalation procedure is associated with the completion status of the activity;

receive an acknowledgement of the completion status after determining that the severity level is a first severity level; and receive a message intended for the patient after determining that the severity level is a second severity level.

34. The computer-program product of claim 31, wherein the instructions further comprise code programmed to:

analyze the status; and provide, to the patient, customized instructions in response to the status.

35. The computer-program product of claim 31, wherein the instructions further comprise code programmed to provide a notification to a provider of the medical treatment relating to the updated patient record.

36. The computer-program product of claim 31, wherein the instructions further comprise code programmed to display tracking metrics that detail the progress of the patient in relation to completing or not completing assigned activities based on the updated patient record.

37. The computer-program product of claim 31, wherein the instructions further comprise code programmed to:

collect data relating to the patient's progress with the program; and analyze the collected data using at least one predefined algorithm, at least one predefined metric, or historical data.

38. The computer-program product of claim 37, wherein the collected data includes data from one or more monitoring devices configured to capture the user's vital readings, including at least one vital reading selected from the group consisting of a heart rate, a blood pressure and a glucose level.

39. The computer-program product of claim 37, wherein the instructions further comprise code programmed to provide the results of the analysis to a third party associated with the medical treatment.

40. The computer-program product of claim 39, wherein the third party comprises a provider of the medical treatment, a physician that performs the medical treatment, or an insurance provider associated with the patient.

41. The computer-program product of claim 31, wherein the completion status is selected from a group of completion statuses comprising a first completion status indicating that the activity was not completed, and a second completion status indicating that the activity was completed with problems.

42. The computer-program product of claim 31, wherein the completion status is selected from a group of completion statuses comprising a first completion status indicating that logon activity is not current, a second completion status indicating that the patient has not reviewed or resolved an alert, and a third completion status indicating that the patient has not recorded or completed the activity.

43. The computer-program product of claim 31, wherein the instructions further comprise code programmed to:

determine, based on historical data relating to a plurality of users, re-admission rates and successful recovery rates on a per-treatment basis over a first period of time.

44. The computer-program product of claim 31, wherein the instructions further comprise code programmed to automatically generate the program for the patient based on a unique result of the medical treatment.

45. The computer-program product of claim 31, wherein the instructions further comprise code programmed to:

provide at least one patient support network tool, wherein the tool provides information to a member of the patent support network to prepare the member to assist the patient to engage the program; and provide a notification to a patient support network of the patient in real time relating to the medical treatment and the program of the patient.

46. A web-based method implemented by at least one computing device for interacting with a user engaging a plan associated with a medical treatment, comprising:

displaying information to the user relating to the plan, wherein the information comprises details for an activity assigned to the user;

receiving status information from the user for the activity;

processing, using one or more computing devices, the status information;

updating a record for the user based on the processed status information;

determining, using the one or more computing devices, whether the activity specified by the digitized content has or has not been properly completed;

determining, using one or more computing devices, a completion status relating to the activity when the collected data indicates that the activity has not been properly completed;

determining, using the one or more computing devices, whether an escalation procedure is associated with the completion status; and sending additional content in response to determining that no escalation procedure is associated with the completion status.

47. A web-based method implemented by at least one computing device for monitoring progress of a user in relation to a plan associated with a medical treatment, comprising:

collecting data relating to the user's progress;

storing the collected data in a database;

analyzing, using one or more computing devices, the collected data;

generating, using the one or more computing devices, a status report regarding the progress of the user in relation to the plan based on the analysis of the collected data;

displaying the status report to at least one additional user who is monitoring the progress of the user;

determining, using the one or more computing devices, that an activity specified by the digitized content has not been properly completed;

determining, using the one or more computing devices, whether an escalation procedure is associated with the activity;

identifying additional content relating to the activity when no escalation procedure is associated with the activity;

sending the additional content in response to determining that no escalation procedure is associated with the activity; and executing the escalation procedure when the escalation procedure is associated with the activity.

* * * * *